United States Patent
Hong et al.

(10) Patent No.: US 10,273,476 B2
(45) Date of Patent: Apr. 30, 2019

(54) MICRORNA-200 BASED APPROACHES FOR MODULATING BONE FORMATION INHIBITION AND BONE REGENERATION

(71) Applicant: UNIVERSITY OF IOWA RESEARCH FOUNDATION, Iowa City, IA (US)

(72) Inventors: Liu Hong, Iowa City, IA (US); Brad Amendt, Iowa City, IA (US); Thad Sharp, Iowa City, IA (US); Aliasger Salem, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/583,564

(22) Filed: May 1, 2017

(65) Prior Publication Data

US 2017/0314020 A1    Nov. 2, 2017

Related U.S. Application Data

(60) Provisional application No. 62/330,113, filed on Apr. 30, 2016.

(51) Int. Cl.
| | | |
|---|---|---|
| *A61K 48/00* | (2006.01) |
| *C07H 21/02* | (2006.01) |
| *C07H 21/04* | (2006.01) |
| *C12N 15/113* | (2010.01) |
| *A61L 27/24* | (2006.01) |
| *A61L 27/56* | (2006.01) |
| *A61L 27/54* | (2006.01) |
| *A61K 31/713* | (2006.01) |
| *A61K 9/16* | (2006.01) |
| *C12N 7/00* | (2006.01) |
| *A61K 9/00* | (2006.01) |
| *A61K 9/51* | (2006.01) |

(52) U.S. Cl.
CPC .......... *C12N 15/113* (2013.01); *A61K 9/0019* (2013.01); *A61K 9/1641* (2013.01); *A61K 9/1647* (2013.01); *A61K 9/5153* (2013.01); *A61K 31/713* (2013.01); *A61L 27/24* (2013.01); *A61L 27/54* (2013.01); *A61L 27/56* (2013.01); *C12N 7/00* (2013.01); *A61K 48/00* (2013.01); *A61L 2300/258* (2013.01); *A61L 2300/412* (2013.01); *A61L 2430/02* (2013.01); *C12N 2310/141* (2013.01); *C12N 2320/31* (2013.01); *C12N 2320/32* (2013.01); *C12N 2330/51* (2013.01); *C12N 2740/15043* (2013.01)

(58) Field of Classification Search
CPC .................... C12N 2310/11; A61K 31/713
See application file for complete search history.

(56) References Cited

U.S. PATENT DOCUMENTS

| | | |
|---|---|---|
| 4,962,091 A | 10/1990 | Eppstein et al. |
| 5,252,701 A | 10/1993 | Jarrett et al. |
| 5,350,674 A | 9/1994 | Boenisch et al. |
| 5,585,362 A | 12/1996 | Wilson et al. |
| 5,980,948 A | 11/1999 | Goedemoed et al. |
| 6,153,212 A | 11/2000 | Mao et al. |
| 6,322,797 B1 | 11/2001 | English et al. |
| 6,419,709 B1 | 7/2002 | Mao et al. |
| 6,485,737 B1 | 11/2002 | English et al. |
| 6,503,538 B1 | 1/2003 | Katsarava et al. |
| 6,583,219 B2 | 6/2003 | Won et al. |
| 6,592,895 B2 | 7/2003 | Lang et al. |
| 6,600,010 B2 | 7/2003 | English et al. |
| 2012/0141419 A1* | 6/2012 | Alferiev et al. ...... C12N 15/113 |

FOREIGN PATENT DOCUMENTS

| | | |
|---|---|---|
| WO | 1994007529 A1 | 4/1994 |
| WO | 2016040347 A2 | 3/2016 |

OTHER PUBLICATIONS

Sangani et al. (Molecular and Cellular Endocrinology, 410, 2015, 19-26).*
Chistiakov et al. (Drug Delivery, 2012, 19(8), 392-405).*
Ebert, et al., "MicroRNA sponges: competitive inhibitors of small RNAs in mammalian cells", Nat Methods 4(9), 721-726 (2007).
Haraguchi, et al., "Vectors expressing efficient RNA decoys achieve the long-term suppression of specific microRNA activity in mammalian cells", Nucleic Acids Res 37(6), e43 (2009).
Penczek, Handbook of Polymer Synthesis, Chapter 17: Phosphorus-Containing Polymers 1077-1132 (Hans R. Kricheldorf ed.) (1992).
Sayed, et al., "MicroRNA-21 Targets Sprouty2 and Promotes Cellular Outgrowths", Mol Biol Cell 19, 3272-3282 (2008).
Scherr, et al., "Lentivirus-mediated antagomir expression for specific inhibition of miRNA function", Nuc Acid Res 35, e149 (2007).
Szoka, et al., "Comparative Properties and Methods of Preparation of Lipid Vesicles (Liposomes),", Ann.Rev. Biophys. Bioeng. 9, 467-508 (1980).

* cited by examiner

*Primary Examiner* — Amy H Bowman
(74) *Attorney, Agent, or Firm* — Viksnins Harris Padys Malen LLP

(57) ABSTRACT

In certain embodiments, the present invention provides the use of microRNA (miR)-200a and/or miR-200c to inhibit ossification and bone formation. In certain embodiments, the present invention provides the use of miR-200a inhibitor to stimulate bone regeneration.

16 Claims, 11 Drawing Sheets
Specification includes a Sequence Listing.

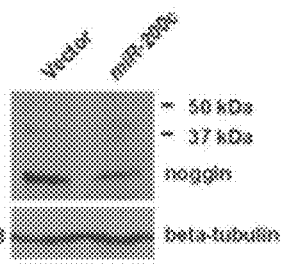
Figure 3A  Figure 3B
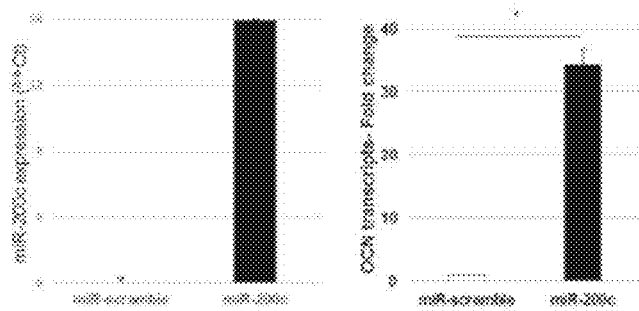
Figure 4A  Figure 4B  Figure 4C
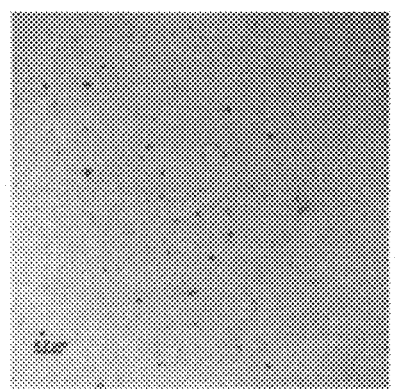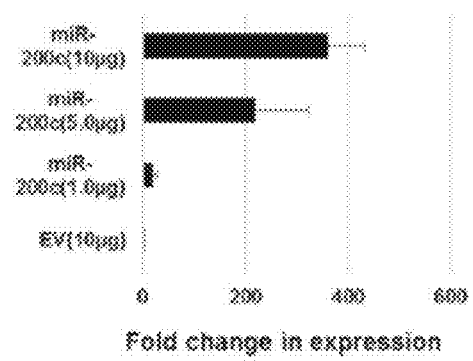
Figure 5A  Figure 5B

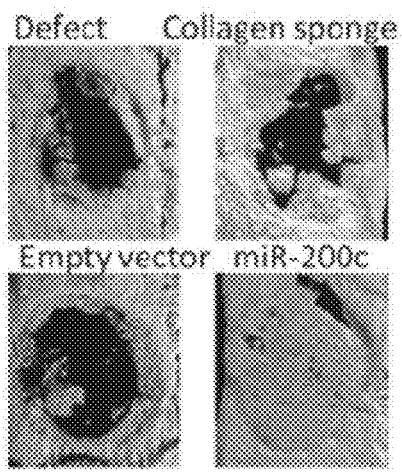
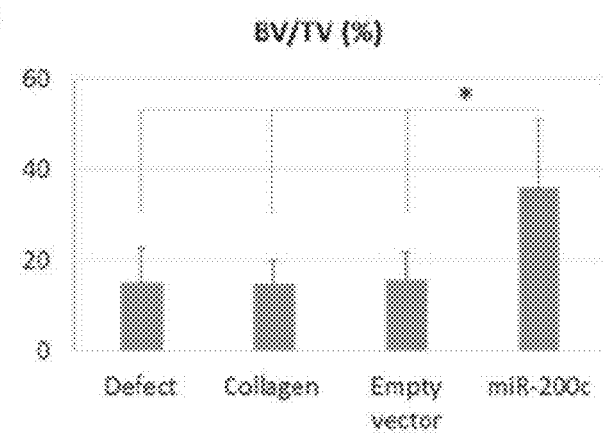
Figure 11A                Figure 11B
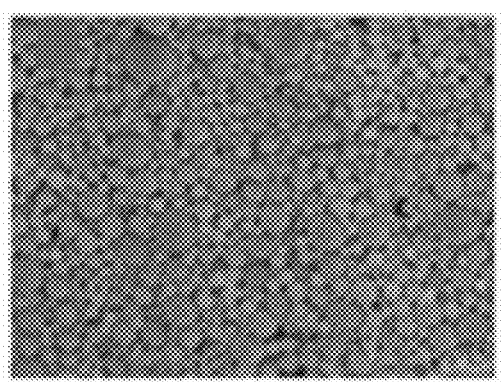
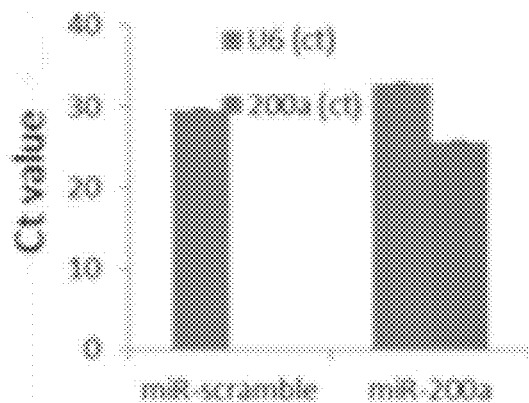
Figure 12A                Figure 12B

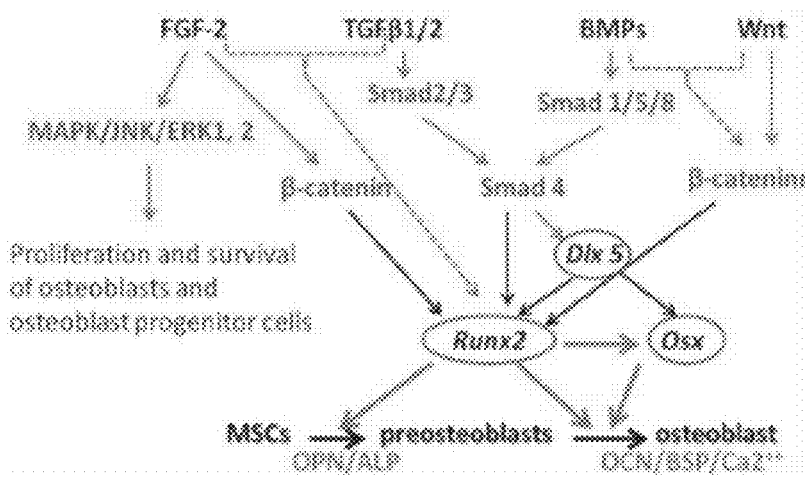
Figure 13
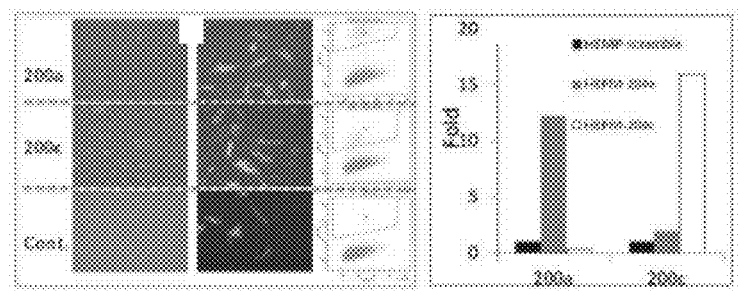
Figure 14A          Figure 14B
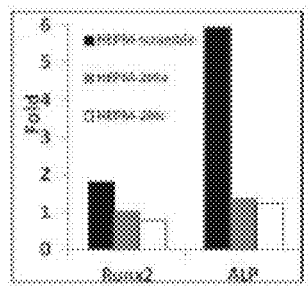   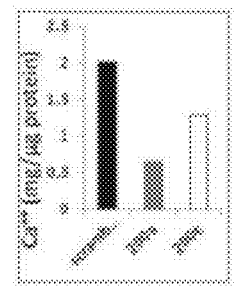
Figure 14C     Figure 14D

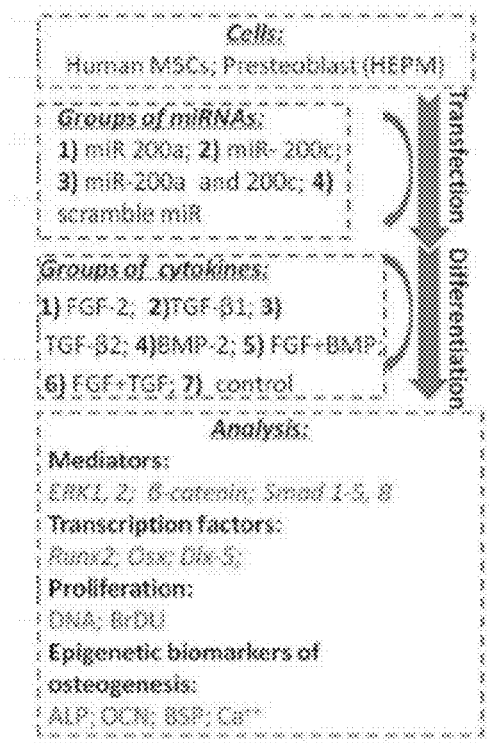
Figure 15A
Figure 15B
Figure 15C
Figure 15D
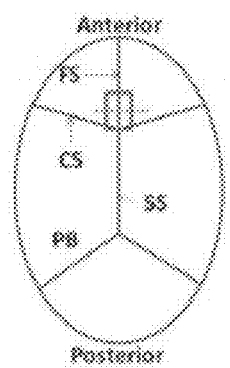 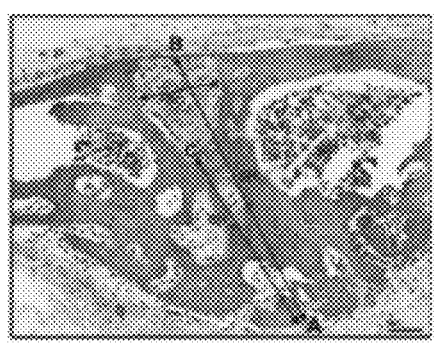
Figure 16A    Figure 16B

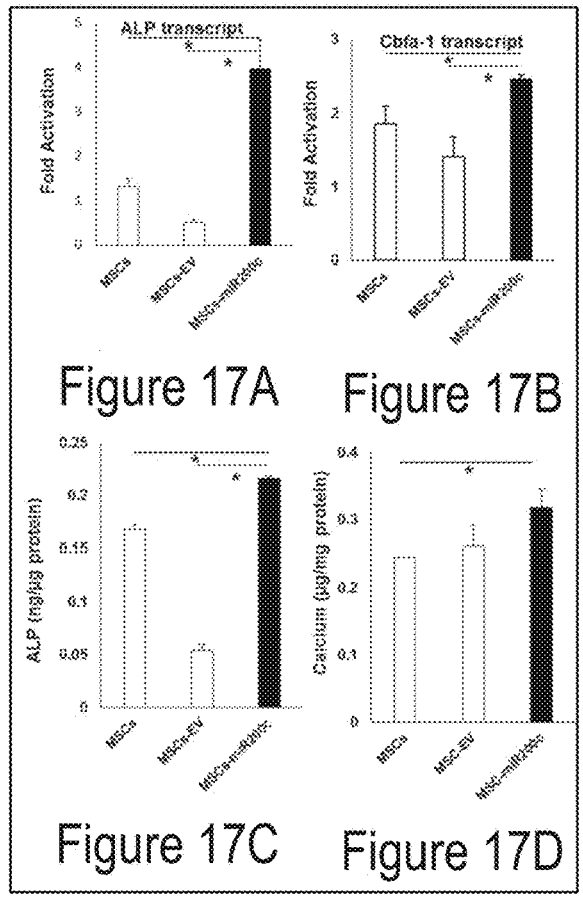
Figure 17A  Figure 17B
Figure 17C  Figure 17D
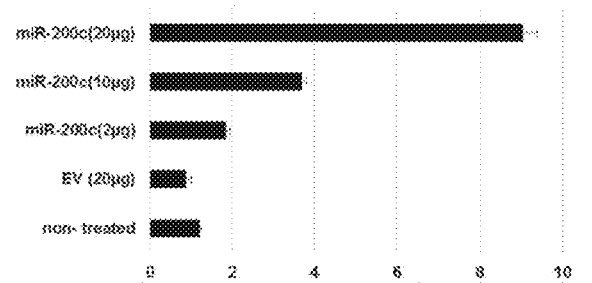
Figure 18A
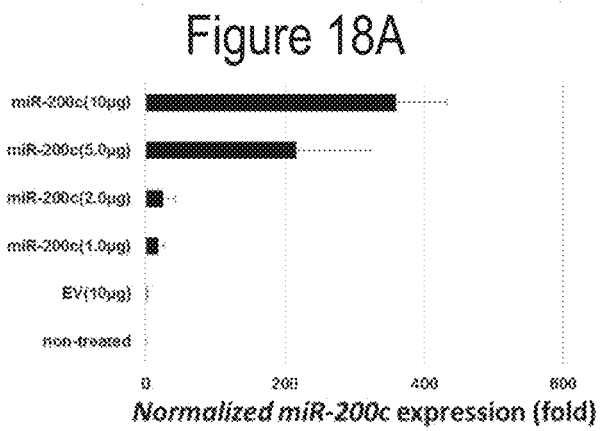
*Normalized miR-200c expression (fold)*
Figure 18B

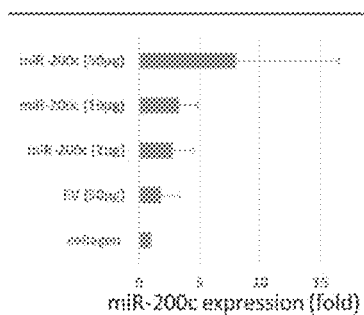 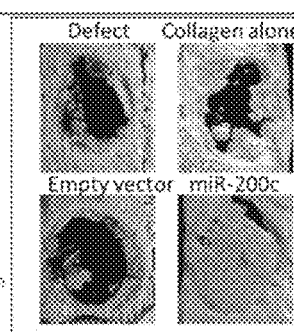 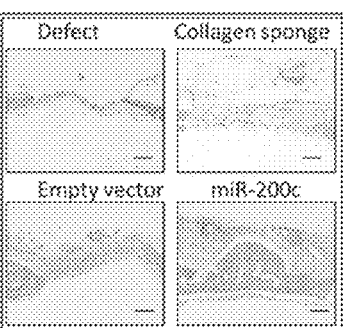
Figure 19A  Figure 19B  Figure 19C
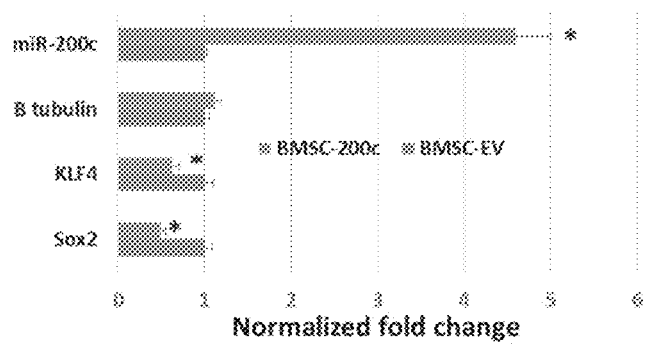
Figure 20A
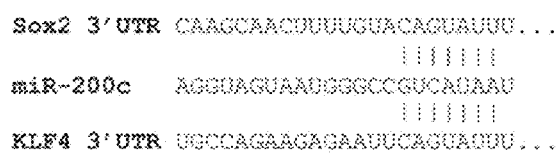
Figure 20B

MICRORNA-200 BASED APPROACHES FOR MODULATING BONE FORMATION INHIBITION AND BONE REGENERATION

CROSS-REFERENCE TO RELATED APPLICATIONS

This application claims priority to U.S. Provisional Application No. 62/330,113 that was filed on Apr. 30, 2016. The entire content of the applications referenced above and hereby incorporated by reference herein.

FEDERAL GRANT SUPPORT

The invention was made with government support under DE024799 and DE025328 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 7, 2017, is named 17023_195US1_SL.txt and is 869 bytes in size.

BACKGROUND OF THE INVENTION

MicroRNAs or miRNAs are short sequences of RNA (20-24 nucleotide molecules) that function by altering the stability or translational efficiency of targeted mRNAs. There has been a significant amount of recent research into miRNAs that has attempted to determine their full scope, mechanism of action and disease association. Products associated with the understanding and clinical application of miRNAs will likely play a strong part in the future of medical care. Given the importance of miRs during different biological processes, tools for repression of miR function may be useful for research and have therapeutic potential. MicroRNAs are thought to regulate tumor progression and invasion via direct interaction with target genes within cells.

Bone grafts are the second most transplanted tissue/material in the United States. Autografts and allografts are the current standard strategies for surgical intervention and subsequent bone repair, but each possesses limitations, such as donor-site morbidity with the use of autograft and the risk of disease transmission with the use of allograft. In order to overcome these inherent limitations, synthetic bone-graft substitutes based on tissue engineering strategies represent an alternative approach. Recombinant human BMP-2 (rhBMP-2), delivered using an absorbable collagen sponge, has been approved by the Food and Drug Administration (FDA) for inducing spinal fusion, fracture healing, and filling bony defects following tumor resection. In dentistry, rhBMP-2 has been used in alveolar ridge and sinus augmentation. Recombinant human BMP-7 (rhBMP-7) is authorized by the FDA as a humanitarian device for use as an autograft alternative for recalcitrant long bone nonunions. There has been a tremendous increase in rhBMP usage as a bone graft substitute in the past few years. In 2009, close to 1.5 billion dollars were spent on bone graft substitutes, half of which was attributed to rhBMPs. However, the outcome of rhBMP treatment may be far from satisfactory. Serious adverse events can occur after the use of rhBMP-2 in oral and maxillofacial procedures. The same study also revealed rising complication rates following BMP-2 administration both in FDA cleared and off-label indications. The high cost associated with rhBMP therapy and the reported adverse events following its usage in supra physiological doses strongly underscore the need to develop an alternative approach that is safer, more cost-effective, and highly efficient for bone regeneration.

One in approximately 2,500 live births in the United States has congenital anomalies collectively called craniosynostosis (premature suture fusion). Children suffering from craniosynostosis may develop severe secondary neurological disorders associated with increased intracranial pressure. The current standard of therapy is resection of fused sutures to release abnormal intracranial pressure and to correct the resulting progressive esthetic deformity. However, this surgical procedure is associated with high morbidity and higher rates of re-synostosis due to an unexpected extremely high osteogenic potential of calvarial bone in craniosynostosis patients. The role of cytokines, especially transforming growth factor (TGF)-β family members and fibroblast growth factors (FGF), participates extensively in suture biology and etiopathogenesis of craniosynostosis. Specifically, FGF-2, TGF-β1, 2, and bone morphometric protein (BMP)-2 have been demonstrated to play critical roles both in pathological and physiological suture osseous fusion by up-regulating the proliferation and differentiation of osteoblasts and their progenitor cells. Therefore, in order to prevent premature sutural osseous fusion there is a critical need to develop novel strategies to inhibit the excessive signaling that are generated by these osteogenic cytokines.

SUMMARY OF THE INVENTION

In certain embodiments, the present invention provides the overexpression of microRNA (miR)-200a to inhibit ossification and bone formation. Overexpression of miR-200a can be used to prevent osseous fusion of cranial sutures in craniosynostosis and inhibit tendon ossification and any other ossification.

In certain embodiments, the present invention provides the use of miR-200a inhibitor to stimulate bone regeneration. MiR-200a inhibitors can be used to enhance osteogenic differentiation and bone formation. There is no microRNA based approach for this application.

BRIEF DESCRIPTION OF DRAWINGS

FIGS. 3A-3B. Noggin inhibition by miR-200c. (FIG. 3A) Normalized luciferase activity of the 3'-UTR Nog-luciferase reporter (WT Nog 3'UTR) with empty plasmid (Vector) or CMV-miR-200c (miR-200c) shows loss of luciferase activity with expression of miR-200c. There is no loss of luciferase activity when the miR-200c seed sequence is mutated (Mut Nog 3'UTR). (FIG. 3B) Western blot analysis shows a decrease in noggin levels when miR-200c is overexpressed in oral epithelial-like cells Beta-tubulin provided a loading control.

FIGS. 4A-4C. mir-200c increases osteogenic biomarkers in a human preosteoblasts. FIG. 4A: Expression of miR-200c in HEPM cells transfected with miR-200c or scrambled miRs. FIG. 4B and FIG. 4C: the amounts of the transcript of OCN (FIG. 4B) and calcium content (FIG. 4C) in HEPM cells with miR-200c or scramble miRs after 1 and 2 weeks, respectively. *: $p<0.05$.

FIGS. 5A-5B. Intracellular delivery of miR-200c using PEI nanoparticles to human bone marrow MSCs. FIG. 5A: TEM image of PEI-mir-200c nanocomplexes. FIG. 5B: Fold change of the transcript of miR-200c in human MSCs transfected with empty vector (EV) (10 μg/per well) and miR-200c (1, 5, 10 μg/per well).

FIG. 6A: Images of ALP and von-Kossa staining in MSCs overexpressing miR-200c. FIG. 6B and FIG. 6C: the transcript of ALP and Cbfa-1 in MSCs overexpressing miR-200c, one week after treatment. FIG. 6D and FIG. 6E: Quantitative measurement of ALP levels and calcium content in MSCs overexpressing miR-200c, one and two week after treatment. Each measurement was made in triplicate.*: $p<0.05$.

FIG. 7A: Images of ALP staining in HEPM cells overexpressing miR-200a, one week after treatment with osteogenic medium (OS) and BMP-2. FIG. 7B and FIG. 7C: ALP levels and calcium content in HEPM cells overexpressing miR-200a, one week after treatment with osteogenic medium and BMP-2. D-F: Normalized expression of the Cbfa-1(FIG. 7D), Twist1 (FIG. 7E), and Msx2 (FIG. 7F) transcripts in HEPM cells infected with miR-200a or the scrambled miRs.*: $p<0.05$.

FIG. 8A: Top-view of mouse skulls using μCT after no treatment, treatment with empty vector, and treatment with miR-200a. FIG. 8B and FIG. 8C: High-resolution top and cross-sectional μCT view of mouse PF sutures after the indicated treatments. FIG. 8D: Microphotographs of cross-sections of PF sutures ad 0.5 mm anterior to the bregma.

FIG. 10A: normal contro; FIG. 10B: LPS treated.

FIGS. 11A-11B. miR-200c improve bone formation in rat calvarial defects. FIG. 11A. Representative μCT scans of regenerated bone tissue after 4 weeks in CBD treated with: empty defects, collagen scaffolds, empty vector-loaded scaffolds, or miR-200c-loaded scaffolds. FIG. 11B: Percentage of BV/TV in DBDs with different treatment (n=4,*:$p<0.05$).

FIGS. 12A-12B. Intracellular delivery of miR-200a using PLGA nanoparticles. FIG. 12A: SEM photograph of miR-200a-loaded PLGA-PEI nanoparticle; FIG. 12B: the Ct value of endogenous control gene (U6) and miR-200a (200a) of HEPM cells 3 days after receiving treatment of miR-200a or scrambled miR-loaded PLGA-PEI nanoparticles.

FIG. 13. Overview of transduction mediators, transcription factors, and epigenetic biomarkers of osteogenic differentiation induced by FGF/TGF/BMP/Wnt signaling.

FIGS. 14A-14D. MiR-200s repressing osteogenic differentiation of preosteoblasts. FIG. 14A: microphotographs and FACsan analysis of HEPM cells after infection of miR-200a and 200c; FIG. 14B: the fold change of miR-200a and 200c expression in HEPM cells after different infection. FIG. 14C: the fold change of gene Runx2 and ALP expression after 1 week cultured in complete DMEM ; FIG. 14D: calcium content after 2 weeks cultured in osteogenic medium. Each measurement was in triplicate.

FIG. 15. Schematic illustration of an experiment designed to determine the effects mediated by miRNAs on FGF/TGF/BMP-induced osteogenic differentiation.

FIGS. 16A-16B. FIG. 16A: Schematic diagram of rodent calvaria. Box indicates site of PF suture. Dashed line denotes the middle plane of PF suture. FS=frontal suture; CS=coronal suture; SS=sagittal suture. FIG. 16B: Micrograph illustrating technique for measurement of bony bridging. A=most inferior (endocranial) point of the suture ridge; B=intersection of line drawn from point A to line connecting the most superior (ectocranial) points of the bony fronts; C=most superior point of bony bridging; SH=suture height, distance from point A to point B; BH=bridging height, distance from point A to point C; SG=suture gap. Bar=40 mm.

FIGS. 17A-17D. Enhancement of osteogenic differentiation of human MSCs with miR-200c overexpression using PEI. FIGS. 17A and 18B: the transcripts of ALP (FIG. 17A) and Runx2 (FIG. 17B) in MSCs overexpressing miR-200c, one week after treatment with osteogenic medium. FIG. 17C and FIG. 17D: Quantitative measurement of ALP levels (FIG. 17C) and calcium content (FIG. 17D) in MSCs with miR-200c. *: $p<0.05$.

FIGS. 18A-18B. Transfection efficiency of miR-200c in human MSCs with treatment of Naked plasmid miR-200c (FIG. 18A) and miR-200c delivered using PEI nanoplexes (FIG. 18B) at different concentrations in vitro.

FIGS. 19A-19C. miR-200c can be transfected in vivo and improve bone formation. FIG. 19A: mR-200c expression in collagen loaded with plasmid miR-200c at different doses after 1 week of implantation. FIG. 19B and FIG. 19C: Representative μCT images and gistologic sections of regenerated bone tissue at rat calvarial defects 4 weeks after different treatments. Bar=500 μm.

FIGS. 20A-20B. miR-200c inhibits Sox2 and Klf4. FIG. 20A: fold change of miR-200c, Sox2 and Klf4 in human MSCs treated with naked plasmid miR-200c. n=3; *:$p<0.05$ vs. BMSC-EV. FIG. 20B. The sequence and miR-200c binding region (SEQ ID NO: 2) located in the 3'UTR of Sox2 (SEQ ID NO: 1) and Klf4 (SEQ ID NO: 3).

FIG. 22A. Images of ALP staining in HEPM cells overexpressing miR-200a, 1 week after treatment with osteogenic medium (OS) or OS with BMP-2. FIG. 22B and FIG. 22C: ALP levels and calcium content in HEPM cells overexpressiong MiR-200a, 1 and 2 weeks after treatment with osteogenic medium and BMP-2. FIG. 22D: Normalized expression of the RUNx2 with miR-200a or the scrambled miRs. *:$p<0.05$. n=3. FIG. 22E: Normalized expression of miR-200a and Pixt2 in human MSCs 4 days after transfection with miR-200a or empty vector (EV). *:$p<0.05$ vs BMSC-EV.

FIG. 23A: Microphotograph of human MSCs 24 hours after treatment with PMIS-200a (Live/Dead staining); FIG. 23B and FIG. 23C: Fold change of PMIS-miR-200a (FIG. 23B) and GFP (FIG. 23C) transcripts in human MSCs 1 week after treatment with PMIS-miR-200a and PMIS-empty vector at 2, 10 and 20 μg/mL. FIG. 23D: Fold change of miR-200a in human MSCs 1 week after treatment with PMIS-miR-200a or miR-200a at 1 μg/mL.

FIG. 24A: microphotograph of the cross-section of sponges of PMIS-200a loaded collagen sponge 1 week after implantation in vivo using IHC staining against GFP. FIG. 24B and FIG. 24C: transcripts of GFP and PMIS-200a in untreated sponges and sponges with PMIS-EV and PMIS-200a after 1 week of implantation. FIG. 24D: Transcripts of OCN and Runx2 in sponges treated with PMIS-200s and PMIS-EV 1 week of implantation. FIG. 24E: Representative μT images. FIG. 24F: The BT/TV of calvarial defects 4 weeks after treatment with PMIS-miR-200a and controls. n=3.

DETAILED DESCRIPTION OF THE INVENTION

Figure 1:
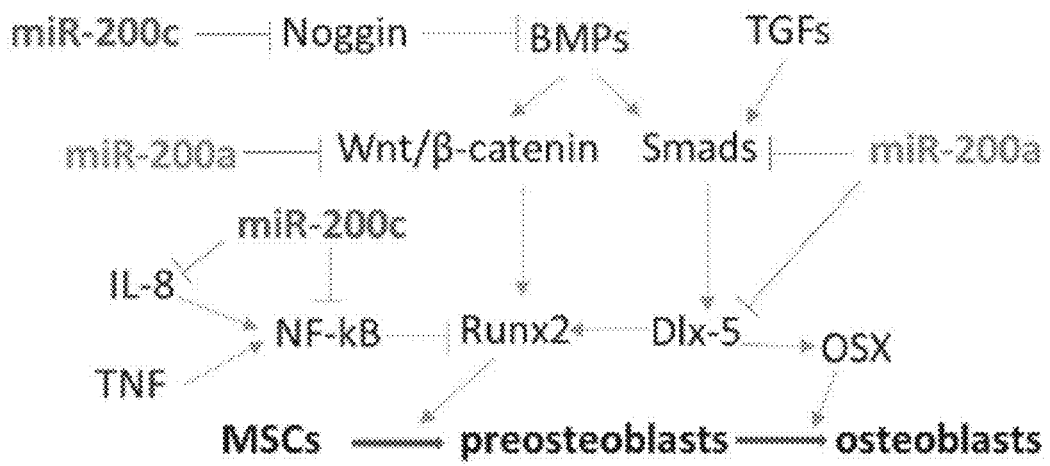
FIG. 1. Potential targets of miR-200a and miR-200c in signal pathways of osteogenesis. →depicts up-regulation; ⊢—depicts down-regulation.
Figure 2:
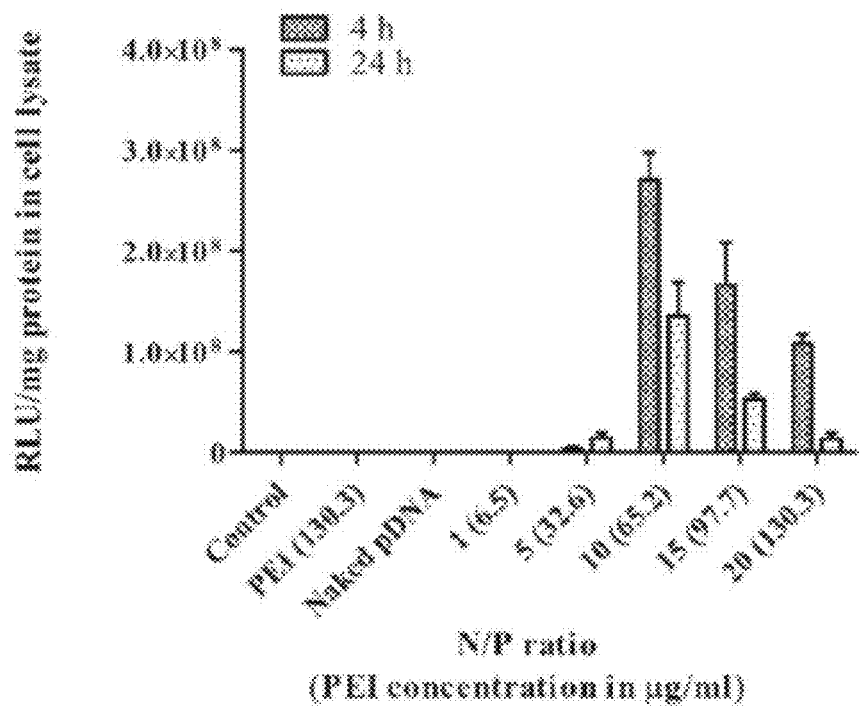
FIG. 2 Luciferase assay assessing the effect of N/P ratio on the transfection capability of PEI-pDNA(encoding for firefly luciferase reporter protein) complexes in MSCs at 4 hours or 24 hours (n=3).

In certain embodiments, the present invention provides a plasmid-based miR inhibitory system (PMIS) based on hairpin structures that uniquely characterize miR transcripts. The addition of short hairpin structure to antisense oligos greatly increased its inhibitory activity, by enhancing the binding of the antisense oligos to miRs. These structures may coordinate physical interactions with proteins that bring the antisense oligo close to the miR and dramatically facilitate their binding. The PMIS expresses anti miR antisense oligos flanked by hairpin structures and contain features including AU rich flanking sequences that are able to enhance miR efficiency of endogenous targets. In addition, the plasmid may be transiently or constitutively expressed depending on the vector or integration.

In certain embodiments, the present invention provides a method of stimulating osteogenic differentiation in a patient in need thereof, comprising administering to the patient a therapeutic composition comprising
  (a) miR-200c or a first expression cassette expressing miR-200c, and/or
  (b) a second expression cassette comprising a second promoter operably linked to a plasmid-based miR-200a inhibitor (PMIS-200a); wherein the therapeutic composition stimulates stimulating osteogenic differentiation in the patient.

In certain embodiments, the therapeutic composition comprises the first expression cassette expressing miR-200c, wherein the miR-200c is operably linked to a first promoter.

In certain embodiments, the first promoter is transiently expressed or is constitutively expressed.

In certain embodiments, the first promoter is a tissue-specific or inducible promoter.

In certain embodiments, the first expression cassette is contained in a first vector.

In certain embodiments, the first vector is a first plasmid.

In certain embodiments, the therapeutic composition comprises the second expression cassette, wherein the PMIS-200a is operably linked to a second promoter.

In certain embodiments, the second promoter is transiently expressed or is constitutively expressed.

In certain embodiments, the second promoter is a tissue-specific or inducible promoter.

In certain embodiments, the second expression cassette is contained in a second vector.

In certain embodiments, the second vector is a second plasmid.

In certain embodiments, the second expression cassette is contained in the first vector.

In certain embodiments, the present invention provides a method of inhibiting osteogenic differentiation of human pre-osteoblasts in a patient in need thereof, comprising administering to the patient a therapeutic composition comprising miR-200a or an expression cassette expressing miR-200a, wherein the therapeutic composition inhibits osteogenic differentiation of human pre-osteoblasts in the patient.

In certain embodiments, the miR-200a is operably linked to a promoter.

In certain embodiments, the expression cassette is contained in a vector.

In certain embodiments, the vector is a plasmid.

In certain embodiments, the vector is a lentiviral vector.

In certain embodiments, the therapeutic composition is contained in biodegradable nanoparticle material.

In certain embodiments, the biodegradable nanoparticle material is polyethylenimine (PEI).

In certain embodiments, the biodegradable nanoparticle material is polylactide-co-glycolide (PLGA).

In certain embodiments, the therapeutic composition is contained in a collagen sponge.

In certain embodiments, the therapeutic composition is administered locally.

In certain embodiments, the therapeutic composition is a sustained release formulation.

In certain embodiments, the osteogenic differentiation bone generates oral, craniofacial, calvarial and/or periodontal bone.

In certain embodiments, the present invention provides a therapeutic composition comprising a plasmid encoding miR-200c and PEI nanoparticles.

In certain embodiments, the therapeutic composition further comprises a plasmid-based miR-200a inhibitor (PMIS-200a).

In certain embodiments, the present invention provides a therapeutic composition comprising a plasmid comprising miR-200a and PEI nanoparticles.

MicroRNAs

MicroRNAs (miRNAs) are small, non-coding RNA molecules, which are able to regulate gene expression posttranscriptionally through degradation of the messenger RNA or inhibition of translation. The total number of different miRNAs is estimated to be approximately 1000-1500. miRNAs thus constitute approximately 1% of the human genome. miRNAs have been discovered in various species and appear to be highly conserved.

Although the target genes (or targets) and thus the biological functions of miRNAs have to date largely not been able to be identified, it is estimated that miRNAs regulate up to 30% of the genes of the human genome.

Firstly, miRNA genes are transcribed by RNA polymerase II into long primary miRNAs (pri-miRNAs). The further processing of these pri-miRNAs takes place in a step-by-step manner and in various compartments. Pri-miRNAs are firstly transformed in the cell nucleus by the RNase III enzyme Drosha into precursor miRNAs (pre-miRNAs) comprising approximately 70-80 nucleotides. Drosha forms a microprocessor complex with the RNA-binding protein DGCR8. Pre-miRNA hairpins are conveyed out of the cell nucleus by the protein exportin-5 and Ran-GTP as cofactor. In the cytoplasm, the pre-miRNA is processed by the RNase II enzyme Dicer to form duplex-miRNAs comprising approximately 22 nucleotides. Dicer interacts in this case with the double-stranded RNA-binding protein TRBP. The miRNA duplex molecules are then unwound, so that mature miRNA is obtained. This mature miRNA is then incorporated in a ribonucleoprotein complex (miRNP), which is very similar to the RNA-induced silencing complex (RISC), the effector molecule of interfering RNA (RNAi) (Hutvagner and Zamore, 2002).

In this form, miRNAs can lead to a downregulation of the respective target gene via two different mechanisms: a) translational inhibition or b) target mRNA cleavage. The choice of mechanism depends on the degree of complementarity between miRNA and the target gene in combination with a so-called Argonaute Protein. In the case of almost perfect complementarity, a cleavage of the target gene takes place with subsequent RNA degradation, whereas a translational inhibition takes place in the case of only partial complementarity.

miRs have been identified as key regulators of progenitor cell differentiation and modulators of cell fate decisions. miRs regulate the fate of stem cells in many different tissues and organs through the specification or differentiation of cell types. miRs can target cell cycle regulators, promote differentiation by inactivating transcriptional repressors, integrate with transcriptional and signaling networks in bone formation, muscle differentiation, neurogenesis, and tooth and craniofacial morphogenesis. The use of miRs in cell reprogramming is a new field of research that has great promise for tooth regeneration.

miR-200 is primarily associated with increased migration/invasion and metastatic activity of various cancer types.

MicroRNA Inhibitor System

In certain embodiments, the present invention provides a microRNA inhibitor system comprising a nucleic acid vector and at least one expression cassette, wherein each expression cassette comprises a promoter operably linked to a miR inhibitor, wherein the miR inhibitor comprises an antisense oligonucleotide (ASO) having a 5' end and a 3' end, and wherein the mirR inhibitor is contiguously linked to a 5' flanking structure at the 5' end and a 3' flanking structure at the 3' end.

In certain embodiments, the vector is a plasmid. In certain embodiments, the vector is a viral vector. In certain embodiments, the vector is an Adenovirus, Adeno-associated virus, lentivirus, baculovirus, or any plasmid incorporated into any virus. In certain embodiments, the plasmids can be yeast, bacterial or mammalian replication competent and low or high copy number plasmids. In certain embodiments the miR Inhibitor is used without a vector as an in vitro transcribed RNA molecule introduced into cells using nano particles, protein systems or transfection reagents. In certain embodiments, the promoters can be Polymerase II or III driven promoters that express both eukaryotic and prokaryotic transcripts, can be either polyadenylated or non-polyadenylated, and any length. In certain embodiments, the plasmids may contain enhancer, silencer, splicing or other regulatory elements.

In certain embodiments, the 5' flanking structure is 5 to 20 nucleotides in length. In certain embodiments, the 5' flanking structure is 15 to 18 nucleotides in length. In certain embodiments, the 5' flanking structure is 17 nucleotides in length.

In certain embodiments, the 3' flanking structure forms a 3' duplex region of 5 to 20 basepairs in length. In certain embodiments, the 3' flanking structure forms a 3' duplex region of 5 to 8 basepairs in length. In certain embodiments, the 3' flanking structure forms a 3' duplex region 7 basepairs in length.

In certain embodiments, the 3' flanking structure is capable of forming a double stranded region with itself and a loop structure, and forms a double stranded region with the 5' flanking structure.

In certain embodiments, the each loop region is independently 6-18 nucleotides in length. In certain embodiments the 5' loop is 15-18 nucleotides in length. In certain embodiments, the middle loop is 8-11 nucleotides in length. In certain embodiments, the 3' loop is 6-12 nucleotides in length.

In certain embodiments, the 5' and/or 3' flanking structure independently encode about 50-90% A or U nucleotides. In certain embodiments, the 5' and/or 3' flanking structure independently encode about 60-90% A or U nucleotides. In certain embodiments, the 5' and/or 3' flanking structure independently encode about 75-85% A or U nucleotides.

In certain embodiments, the ASO is 18 to 26 nucleotides in length.

In certain embodiments, the promoter is a transiently expressed. In certain embodiments, the promoter is constitutively expressed. In certain embodiments, the promoter is a polII or polIII promoter. In certain embodiments, the polIII promoter is a U6 promoter. In certain embodiments, the polIII promoter is a mouse U6 promoter. In certain embodiments, the promoter is a polII promoter. In certain embodiments, the promoter is a tissue-specific promoter. In certain embodiments, the promoter is an inducible promoter.

In certain embodiments, 3' flanking structure ends in an A nucleotide.

In certain embodiments, the nucleic acid is DNA.

In certain embodiments, the ASO is completely complimentary to a miR and binds with an affinity having a Kd equal or less than 100+/−5 nM.

In certain embodiments, the microRNA inhibitor system comprises multiple expression cassettes.

In certain embodiments, the microRNA inhibitor system further comprises a promoter operably linked to a reporter gene.

In certain embodiments, the seed sequence of the ASO is identical to the seed region of the target miR.

In certain embodiments, the 5' flanking structure is 17 nucleotides in length, wherein the 3' flanking structure forms a 3' duplex region 7 basepairs in length, wherein the 5' and 3' flanking structures independently include about 75-85% AU sequences, and wherein the 3' flanking structure ends in an A nucleotide.

MiR Inhibitors

In certain embodiments, the present invention provides a miR inhibitor of about 100 to 135 nucleotides in length, comprising an antisense oligonucleotide (ASO) having a 5' end and a 3' end, and wherein the mirR inhibitor is contiguously linked to a 5' flanking structure at the 5' end and a 3' flanking structure at the 3' end, wherein, the 3' flanking structure forms a double stranded region with itself and a loop structure, and forms a double stranded region with the 5' flanking structure.

In certain embodiments, the 5' and/or 3' hairpin structure independently encode about 50-90% A or U nucleotides. In certain embodiments, the 5' and/or 3' flanking structure independently encode about 60-90% A or U nucleotides. In certain embodiments, the 5' and/or 3' flanking structure independently encode about 75-85% A or U nucleotides.

In certain embodiments, the ASO is 18 to 26 nucleotides in length. In certain embodiments, 3' flanking structure ends in an A nucleotide.

In certain embodiments, the ASO is antisense to a miR and binds with a Kd equal or less than 100+/−5 nM.

In certain embodiments, the miR inhibitor further comprises a promoter operably linked to a reporter gene. In certain embodiments the miR Inhibitor is used without a vector as an in vitro transcribed RNA molecule introduced into cells using nano particles, protein systems or transfection reagents.

Methods of Inhibiting miR

In certain embodiments, the method of inhibiting miR comprising administering the system described above, wherein the system reduces the level of target miR by about 25% to 100%. In certain embodiments, the system reduces the level of target miR by about 90%.

In certain embodiments, the ASO irreversibly silences its target miRs. In certain embodiments, the target miR is miR-200a.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides "Operably-linked" refers to the association two chemical moieties so that the function of one is affected by the other, e.g., an arrangement of elements wherein the components so described are configured so as to perform their usual function.

Currently, one way to attenuate miR activity is administration of antisense oligos into cells that compete for binding with endogenous targets. A limitation of the currently used miR inhibitors resides in their inability to be retained in the tissues after cell division and they must be reapplied to maintain their effectiveness. To address these limitations and promote long-term repression of specific miRs, several plasmid and/or viral vectors expressing antagomirs, sponges, eraser and Tough Decoy (TuD) RNA molecules have been reported (Scherr, M. et al. Lentivirus-mediated antagomir expression for specific inhibition of miRNA function. *Nuc. Acid Res.* 35, e149 (2007); Sayed, D. et al. MicroRNA-21 targets Sprouty2 and promotes cellular outgrowths. *Mol. Biol. Cell* 19, 3272-3282 (2008); Ebert, M. S., Neilson, J. R. & Sharp, P. A. MicroRNA sponges: competitive inhibitors of small RNAs in mammalian cells. *Nature Methods* 4, 721-726 (2007); Haraguchi, T., Ozaki, Y. & Iba, H. Vectors expressing efficient RNA decoys achieve the long-term suppression of specific microRNA activity in mammalian cells. *Nuc. Acid Res.* 37, e43 (2009)).

In certain embodiments, the present invention provides a plasmid-based miR inhibitor system (PMIS) based on hairpin structures that uniquely characterize miR transcripts, that inhibits miR activity in cells and mice. The PMIS engineered optimal secondary structure and flanking sequences form a stable complex with the miR, Argonaute and Dicer proteins. The addition of short hairpin structure to antisense oligos greatly increased its inhibitory activity, by enhancing the binding of the antisense oligos to miRs. The miR Inhibitor can be used as an in vitro transcribed RNA molecule without the need for a vector to express it in cells. The RNA miR inhibitor molecule can be introduced into any cell, tissue or living organism without a vector to inhibit microRNAs.

In cells, one PMIS can effectively inhibit miR family members that share the same seed sequence. The PMIS system can dissect different functions of miRs within miR cluster.

This is a new tool to study the role of miR regulation during development in animals, in cells and tissues, and as a therapeutic reagent in cancer and other diseases with little or no toxicity, induced long-term repression of miRNA, and has a low cost.

Promoters

The present invention further provides an expression cassette containing a promoter contiguously linked to a nucleic acid described herein. In certain embodiments, the promoter is a polII or a polIII promoter, such as a U6 promoter (e.g., a mouse U6 promoter). In certain embodiments, the expression cassette further contains a marker gene. In certain embodiments, the promoter is a polII promoter. In certain embodiments, the promoter is a tissue-specific promoter. In certain embodiments, the promoter is an inducible promoter. In certain embodiments, the promoter is a polIII promoter. In certain embodiments, the promoter is an inducible promoter. In certain embodiments, the expression cassette uses a constitutive promoter, tissue-specific promotes, development-specific promotes, regulatable promoter or viral promoter.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example, an miRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence," i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted herein, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1 RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated," they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=-4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted herein, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation: Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from a source by chemical means, e.g., by the use of restriction endonucleases, so that it can be further manipulated, e.g., amplified, for use in the invention, by the methodology of genetic engineering. "Recombinant DNA" includes completely synthetic DNA sequences, semi-synthetic DNA sequences, DNA sequences isolated from biological sources, and DNA sequences derived from RNA, as well as mixtures thereof.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed. The described miR Inhibitor can also be introduced into host cells as an in vitro transcribed RNA molecule, without the use of a vector. This miR Inhibitor RNA molecule works exactly like the Plasmid-Based miR Inhibitor to inhibit microRNA function.

Physical methods to introduce a preselected DNA into a host cell include calcium phosphate precipitation, lipofection, particle bombardment, microinjection, electroporation, nanoparticles and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed herein, a "transfected" "or" "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR and/or Northern blotting may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into a miR inhibitor.

Methods for Introducing the Expression Cassettes of the Invention into Cells

The inhibitory nucleic acid material (e.g., an expression cassette encoding a miR inhibitor) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, nanoparticles, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the miR inhibitor together with a promoter to control transcription. The promoter characteristically has a specific nucleotide sequence necessary to initiate transcription. The exogenous nucleic acid material may further include additional sequences (i.e., enhancers) required to obtain the desired transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of miR inhibitor generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a miR inhibitor sequence that are in the cell.

In addition to at least one promoter and at least one heterologous nucleic acid sequence encoding the miR inhibitor, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the miR inhibitor (s), the other vector containing a selection gene. The selection of a suitable promoter, enhancer, selection gene, and/or signal sequence is deemed to be within the scope of one of ordinary skill in the art without undue experimentation.

The following discussion is directed to various utilities of the instant invention. For example, the instant invention has utility as an expression system suitable for silencing the nucleic acid sequence of interest.

The instant invention also provides methods for genetically modifying cells of a mammalian recipient in vivo. According to one embodiment, the method comprises introducing an expression vector for expressing a miR inhibitor sequence in cells of the mammalian recipient in situ by, for example, injecting the vector into the recipient.

Delivery Systems for Delivering microRNAs and PMIS microRNA Inhibitors to Human and Murine Cells and Tissues A wide range of nano-sized complexes, nanoparticles, microparticles and lipid based delivery systems are used to deliver microRNAs and PMIS microRNA inhibitors to human and murine cells and tissues. These include synthetic cationic polymers such as polyethylenimine and natural polymers such as chitosan that can form complexes with the PMIS and microRNAs. The PMIS and microRNAs can be loaded into cationic, anionic and neutral liposomes. Also, the PMIS and microRNAs can be loaded into biodegradable synthetic polymers such as polylactide-co-glycolide (PLGA), PLA, polycaprolactone (PCL), polyanhydrides (PA). This list of provided materials is not exhaustive and we often use combinations and permutations of these materials such as preparing PLGA and Polyethylenimine (PEI). A wide range of cell binding or cell targeting ligands can be conjugated to these delivery systems including (but not limited to) transferrin, cell penetrating peptides like RGD or TAT, aptamers, galactose and mannose.

A polymeric microparticle core as described herein can comprise one or more polymers. Polymers can be selected from the group consisting of biocompatible and/or biodegradable polymers. As used herein, the term "biodegradable" refers to the ability of a composition to erode or degrade in vivo to form smaller chemical fragments. Degradation may occur, for example, by enzymatic, chemical or physical processes. Non-limiting examples of biodegradable polymers that can be used in aspects of the invention include poly(lactide)s, poly(glycolide)s, poly(lactic acid)s, poly(glycolic acid)s, poly (lactide-co-glycolide), polyanhydrides, polyorthoesters, polycaprolactone, polyesteramides, polycarbonate, polycyanoacrylate, polyurethanes, polyacrylate, blends and copolymers thereof.

Other additional biodegradable polymers include biodegradable polyetherester copolymers. Generally speaking, the polyetherester copolymers are amphiphilic block copolymers that include hydrophilic (for example, a polyalkylene glycol, such as polyethylene glycol) and hydrophobic blocks (for example, polyethylene terephthalate). An exemplary block copolymer is, but is not limited to, poly(ethylene glycol)-based and poly(butylene terephthalate)-based blocks (PEG/PBT polymer) and PLGA. PEG/PBT polymers are commercially available from OctoPlus Inc, under the trade designation PolyActive™. Non-limiting examples of biodegradable copolymers or multiblock copolymers include the ones described in U.S. Pat. Nos. 5,980,948 and 5,252,701, the contents of which are incorporated herein by reference in their entirety.

Other biodegradable polymer materials include biodegradable terephthalate copolymers that include a phosphorus-containing linkage. Polymers having phosphoester linkages, called poly(phosphates), poly(phosphonates) and poly (phosphites), are known in the art. See, for example, Penczek et al., Handbook of Polymer Synthesis, Chapter 17: "Phosphorus-Containing Polymers," 1077-1 132 (Hans R. Kricheldorf ed., 1992), as well as U.S. Pat. Nos. 6,153,212; 6,485,737; 6,322,797; 6,600,010; 6,419,709; 6,419,709; 6,485,737; 6,153,212; 6,322,797 and 6,600,010, the contents of which are incorporated herein by reference in their entirety.

Biodegradable polyhydric alcohol esters can also be used for the purposes of the invention (See U.S. Pat. No. 6,592,895, which is incorporated herein by reference in its entirety). In some embodiments, the biodegradable polymer can be a three-dimensional crosslinked polymer network containing hydrophobic and hydrophilic components which forms a hydrogel with a crosslinked polymer structure, such as the one described in U.S. Pat. No. 6,583,219. In yet further embodiments, the biodegradable polymer can comprise a polymer based upon α-amino acids (such as elastomeric copolyester amides or copolyester urethanes, as described in U.S. Pat. No. 6,503,538, which is incorporated herein by reference in its entirety).

In one embodiment, the polymeric microparticle core described herein comprises poly(lactide-co-glycolide) (PLGA). In certain embodiments, the polymeric microparticle core described herein comprises at least about 20%, at least about 30%, at least about 40%, at least about 50%, at least about 60%, at least about 70%, at least about 80%, at least about 90%, at least about 95%, about 98%, about 99% or 100% of PLGA.

In general, any biocompatible material well known in the art for fabrication of microparticles can be used in embodiments of the microparticle described herein. Accordingly, a microparticle comprising a lipidic microparticle core is also within the scope of the invention. An exemplary lipidic microparticle core is, but is not limited to, a liposome. A liposome is generally defined as a particle comprising one or more lipid bilayers enclosing an interior, e.g., an aqueous interior. In one embodiment, a liposome can be a vesicle formed by a bilayer lipid membrane. Methods for the preparation of liposomes are well described in the art, e.g., Szoka and Papahadjopoulos (1980) Ann. Rev. Biophys. Bioeng. 9: 467, Deamer and Uster (1983) Pp. 27-51 In: Liposomes, ed. M. J. Ostro, Marcel Dekker, New York, and the like.

The cationic dendrimer as described herein is generally a repeatedly branched and roughly spherical molecule with one or more positively-charged functional groups. In one embodiment, the cationic dendrimer is symmetric around the core, and generally adopts a roughly spherical three-dimensional morphology. In a particular embodiment, the cationic dendrimer used for surface modification of the microparticle core is poly(amidoamine) or PAMAM. The core of PAMAM is a diamine (commonly ethylenediamine), which is reacted with methyl acrylate, and then another ethylenediamine to make the generation-0 (G-0) PAMAM. Successive reactions create higher generations, which tend to have different properties. Lower generations can be considered as flexible molecules with no appreciable inner regions, while medium sized (G-3 or G-4) can have internal space that is essentially separated from the outer shell of the dendrimer. Very large (G-7 and greater) dendrimers can be considered as roughly solid particles with very dense surfaces due to the structure of their outer shell. In one embodiment, the outer surface of the microparticle core is modified with PAMAM Generation-3.

Without limitations, in some embodiments, other positively-charged polymer molecules can also be used to modify the outer surface of the microparticle core described herein. Examples of positively-charged polymers include, but are not limited to, polyamino acids such as polylysine, polyhistidine, polyornithine, polycitrulline, polyhydroxylysine, polyarginine, polyhomoarginine, polyaminotyrosine, and protamines. Other suitable positively-charged polymers include, but are not limited to, polydiaminobutyric acid, polyethyleneimine, polypropyleneimine, polyamino(meth)acrylate, polyaminostyrene, polyaminoethylene, poly(aminoethyl)ethylene, polyaminoethylstyrene, diethyl amino ethyl cellulose, poly-imino tyrosine, cholestyramine-resin, poly-imino acid, 1,5-dimethyl-1,5-diazaundecamethylene polymethobromide (hexadimethrine bromide), chitosan, poly(amidoamine) dendrimers, and combinations thereof.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art. As used herein, the term "therapeutic miR inhibitor" refers to any siRNA that has a beneficial effect on the recipient. Thus, "therapeutic miR inhibitor" embraces both therapeutic and prophylactic miR inhibitor.

Administration of miR inhibitor may be accomplished through the administration of the nucleic acid molecule encoding the siRNA. Pharmaceutical formulations, dosages and routes of administration for nucleic acids are generally known.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Examples.

EXAMPLE 1

It has been reported that approximately 50% of American adults aged 30 years and older have periodontitis and half of them have alveolar bone loss. Periodontal bone defects may eventually lead to tooth loss and osseointegration failure of dental implants. The efficacy of current treatments, including anti-resorptive and anabolic agents, to arrest and restore periodontal bone defects is limited. There is strong evidence that the majority of periodontitis-induced bone loss occurs mainly as a result of activation of host-derived immune and inflammatory defense mechanisms. Imbalance and dysregulation of proinflammatory molecules and cytokine networks play essential roles in the process of periodontitis and associated bone resorption. These inflammatory factors also inhibit osteogenic differentiation and bone formation. Thus, simultaneously reducing proinflammatory cytokines and increasing osteogenic differentiation represents a new strategy for developing a novel therapeutic tool to arrest bone loss and restore periodontal bone defects.

Function of microRNA-200 families on osteogenesis and inflammation. MicroRNAs (miRs) are small non-coding RNAs that promote the degradation and/or repress the translation of mRNA through sequence specific interactions with the 3' UTRs of specific mRNA targets. miRs participate in many aspects of physiologic homeostasis, including cell differentiation, proliferation, apoptosis, and important metabolic pathways. miR-200a and miR-200c, members of the miR-200 family, have recently been demonstrated to be involved in osteogenic differentiation, bone development, and inflammation. Specifically, miR-200c inhibits Noggin expression by directly targeting its 3'UTR, which indicates its potential for improving osteogenic differentiation and bone formation. In addition, it has been demonstrated that miR-200c executes inhibitory regulation in signal pathways of NF-kB and reduces levels of multiple proinflammatory cytokines, including IL-8, IL-6 and CCL-6, by targeting their 3'UTRs. Overexpression of miR-200c significantly promotes osteogenic differentiation in preosteoblasts and human MSCs. The data also show that plasmid miR-200c, loaded in collagen sponges, increases bone formation in calvarial defects of rats. Relatedly, miR-200a has been demonstrated to inhibit osteogenic differentiation and bone formation. Specifically, miR-200a directly suppresses β-catenin/Wnt signaling by targeting the β-catenin mRNA, and suppresses expression of the TGF-β2/Smad pathway by targeting Smad-interacting proteins. miR-200a may also inhibit BMP-2-induced osteogenic differentiation by targeting the expression of distal-less homeobox5 (Dlx5). miR-200a suppresses the osteogenic capacities of human preosteoblasts by down-regulating relevant transcription factors. Moreover, miR-200a can significantly reduce osseous fusion of cranial suture during mouse development. This evidence strongly supports using miR-200c expression and miR-200a inhibition to develop a novel, miR-based therapeutic approach for bone regeneration of craniofacial and periodontal bone defects.

Synthetic bone-graft substitutes are a promising alternative approach to current standard treatments for oral and craniofacial bone defects. MicroRNAs (miRs) are small non-coding RNAs that have emerged as important transcriptional regulators in both physiologic and pathophysiological conditions. It has been previously shown that members of the miR-200 family actively regulate osteogenic differentiation, bone development, and inflammation, indicating a potential use for these miRs in developing novel therapeutics for bone regeneration of craniofacial and periodontal bone defects.

A miR-based gene therapy program has been developed that can be used to effectively promote osteogenic differentiation and bone regeneration for restoring oral and craniofacial bone defects. By overexpressing miR-200c and inhibiting miR-200a using an efficient non-viral delivery system, osteogenic differentiation and bone formation can effectively be enhanced, significantly improving the efficacy of bone morphometric proteins (BMPs) on bone regeneration. The data below demonstrate that: 1) miR-200a directly suppresses β-catenin/Wnt signaling and inhibits BMP-2-induced osteogenic differentiation by targeting Dlx-5, and miR-200a inhibits osteogenic differentiation of human preosteoblasts and postpones bone formation at the cranial suture during development; 2) miR-200c inhibits Noggin, and that overexpression of miR-200c acts to increase osteogenic differentiation of human preosteoblasts and bone marrow mesenchymal stem cells (MSCs), and that miR-200c also inhibits the NF-kB signal pathway and directly targets a number of proinflammatory cytokines; 3) polyethylenimine (PEI) nanoparticles have been developed as a non-viral vector to efficiently transfect plasmid DNA for bone regeneration. This system transfects plasmid miR-200c to human MSCs and enhances osteogenic differentiation. Also poly lactic-co-glycolic acid (PLGA) nanoparticles have been developed that can sustain the release of PEI-pDNA nanoplexes. Plasmid miR-200c and a plasmid-based miR-200a inhibitor (PMIS-200a) delivered using optimized biodegradable nanoparticles significantly promotes osteogenic differentiation and regenerate bone in oral and craniofacial defects.

FIG. 1 summarizes the signal pathways hypothetically targeted by miR-200a and miR-200c in affecting osteogenesis. Polyethylenimine (PEI) nanoparticles as a non-viral vector have been demonstrated to transfect miRs into human primary cells. A novel alternative substitute to bone-grafting using plasmid miR-200c and a plasmid-based miR-200a inhibitor system (PMIS-200a) delivered by biodegradable nanoparticles is developed.

miR-200c knockout mice exhibit tooth and bone defects, indicating the important role of miR-200c in bone development. As described below, overexpression of miR-200c can effectively improve osteocalcin (OCN) and calcium content in human preosteoblasts. Thus, miR-200c may be used to improve osteogenic differentiation and promote bone regeneration for clinical application. A safe gene delivery system to efficiently deliver miR-200c and optimize its function is needed. PEI nanoparticles have been used as a non-viral vector for gene delivery due to their "proton-sponge" effect and high transfection efficiency. It has also been shown that it is possible to intracellularly deliver plasmid DNA using PEI nanoparticles. Studies described below also show that PEI can effectively deliver plasmid miR-200c into human bone marrow MSCs and significantly improve the biomarkers of osteogenic differentiation in these MSCs. and let-7, as controls to compare and determine the capacity of miR-200c.

Overexpression of miR-200c promotes osteogenic differentiation in human preosteoblasts. miR-200c was transduced into human embryonic palatal mesenchyme cells (HEPM), a preosteoblast cell line, using lentiviral vectors. The cells with scrambled miRs were used as controls. The expression of miR-200c in the cells after transduction with miR-200c is 15.9±0.1 (delta/delta Ct) higher than that of controls (FIG. 4A). The cells were then cultured in DMEM medium supplemented with β-glycerophosphate (1 mM) and ascorbic acid (5 mg/ml) up to 2 weeks. After one week, OCN transcripts measured using real-time PCR in miR-200c overexpression cells were 30-fold higher than control cells with scrambled miRs (FIG. 4B). The calcium content in miR-200c cells was three times higher than that of cells with scrambled miRs after two weeks (FIG. 4C).

Figure 6A:
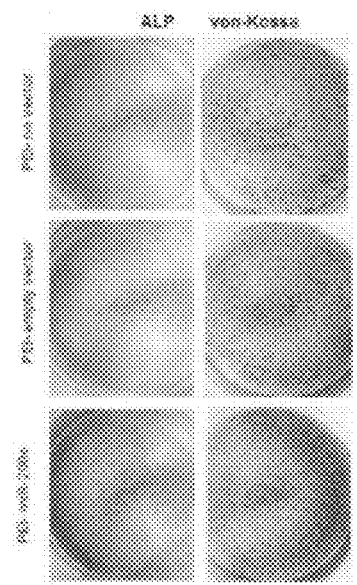
FIGS. 6A-6E. Enhancement of osteogenic differentiation of human bone marrow MSCs with overexpression of miR-200c using PEI nanoparticles.
Figure 6B:
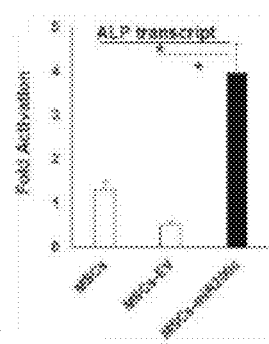
Figure 6C:
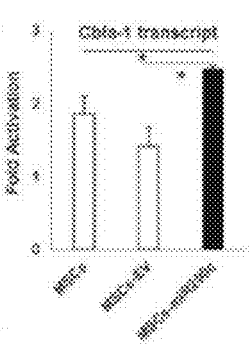
Figure 6D:
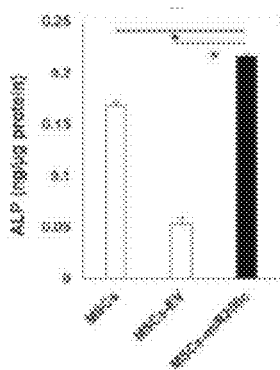
Figure 6E:
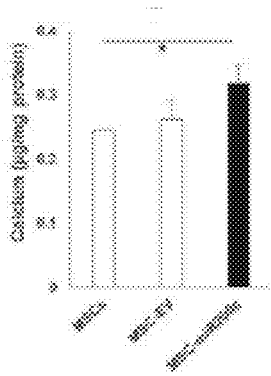

PEI nanoparticles deliver miR-200c into human bone marrow MSCs and enhance osteogenic differentiation of MSCs. Plasmid miR-200c was incorporated into PEI to form nanoplexes at an N/P ratio of 10:1. The encapsulation efficiency and plasmid miR-200c condensation within the complex were elucidated using spectrophotometry and gel electrophoresis, respectively. PEI-miR-200c nanoplexes were visualized using TEM (FIG. 5A). In order to test the transfection efficiency, 1, 2, 5, and 10 μg PEI-miR-200c nanoplexes were added into the medium of cultured human MSCs in a 6-well plate. PEI-empty vector (10 μg) was used as a control. The medium was exchanged after 4 hours to remove extra nanoplexes. After one week miR-200c overexpression in a dose-dependent manner was detected using real-time PCR analysis in the cells treated with PEI-miR-200c nanoplexes (FIG. 5B). In order to test the capabilities of miR-200c to improve osteogenic differentiation, human bone marrow MSCs in 6-well plate were transfected using PEI-miR-200c or PEI-empty vector at 1.0 μg/per well, the cells were subsequently cultured using DMEM supplemented with ascorbic acid and β-glycerophosphate up to 2 weeks. PEI-miR-200c transfected cells showed stronger ALP and von-Kossa staining than that in controls, including MSCs with and without treatment with the PEI-empty vector (FIG. 6A). Quantitatively, the transcripts of ALP (FIG. 6B) and Cbfa-1 (FIG. 6C) are significantly increased in the cells treated with PEI-miR-200c, compared to controls including MSCs treated with PEI, with or without empty vector. In addition, the ALP concentration (FIG. 6D) and calcium content (FIG. 6E) in the MSCs transfected with miR-200c was increased after two weeks in culture.

Synthesis and characterization of PEI-miR-200c nanoplexes: In order to optimize the biocompatibility and transfection efficiency, PEI nanoparticles encapsulating plasmid miR-200c with a range (1, 5, 10, 16, and 21) of N/P ratios are synthesized. The effect of N/P ratio of PEI-miR-200c nanoplexes on their encapsulation efficiency, cytotoxicity, and transfection efficiency are evaluated. After the synthesis of PEI-miR-200c nanoplexes, the size and polydispersity of the synthesized nanoplexes are determined using dynamic light scattering and transmission electron. Zeta potential (surface charge) that is based on the electrophoretic mobility of the nanoplexes using folded capillary cells is determined using the laser scattering method. The encapsulation efficiency and plasmid miR-200c condensation within the complex is elucidated using spectrophotometry and gel electrophoresis, respectively.

Biocompatibility and transfection efficiency of PEI-miR-200c nanoplexes: To test cytotoxicity, human bone marrow MSCs is seeded at 10,000 cells/per well in a 96-well plate and treated with PEI-miR-200c nanoplexes at different N/P ratios. Untreated cells act as controls, while cells treated with high dose PEI are used as a positive control to induce cytotoxicity. The same amount of PEI-empty vector is also included as a control. The cytotoxicity of PEI-miR-200c nanoplexes is determined using MTT assay after 4 and 24 hrs. To test transfection efficiency human MSCs are seeded at $10^5$ cells/per well in a 6-well plate and treated with 1 μg of PEI-miR-200c nanoplexes with different N/P ratios. The expression of miR-200c is determined by real-time PCR after 48 hrs.

Osteogenic differentiation of human MSCs by miR-200c overexpression: Human bone marrow MSCs (Lonza) in a 6-well plate is treated with PEI alone, miR-200c alone, PEI-miR-200c nanoplexes, and PEI-empty vector nanoplexes at 1, 2, 5, 10 μg at a N/P ratio of 10. The N/P ratio of PEI-miR-200c is adjusted as needed. The cells then are cultured in osteogenic medium consisting of DMEM medium supplemented with ascorbic acid (5 mg/ml) and glycerophosphate (5 mM) and lysed at 48, 72 and 96 hrs. The biomarkers of osteogenic differentiation, including Noggin, BMP-2, BMP-7, ALP, Runx2, collagen type I, OCN, bone sialoprotein (BSP), and Osterix transcripts are determined using real-time PCR. In addition, ALP activity, the protein of OCN, BSP, collagen type 1 and calcium content of transfected MSCs are quantitated after 1 and 2 weeks.

Comparison of osteogenic differentiation mediated by miR-200c and other miRs: Human bone marrow MSCs in a 6-well plate are treated with PEI alone, the nanoplexes of PEI incorporating miR-200c, miR-26a, miR-148b, miR-29b, let-7, and empty vector at 5 μg/per well at an N/P ratio of 10. These miRs have been demonstrated to enhance osteogenic differentiation and bone regeneration. The dose of miRs and N/P ratio is adjusted as needed. The cells then are differentiated and the biomarkers of osteogenic differentiation will be analyzed.

Synergistic function of miR-200c on osteogenic differentiation induced by BMP-2: Human bone marrow MSCs in a 6-well plate are treated with the different combinations of PEI-miR-200c nanoplexes at 1 or 5 μg/per well at a N/P ratio of 10 with rhBMP-2 at 1 or 5 μg/per well, respectively. PEI-empty vector nanoplexes at the same dose and N/P ratio serve as controls. The N/P ratio and doses of PEI-miR-200c are adjusted as needed. The cells then are differentiated and the biomarkers of osteogenic differentiation are analyzed.

Molecular function of miR-200c in human MSCs: The function of miR-200c in BMP-associated signaling pathway is evaluated during osteogenic differentiation. MSCs are treated with PEI-miR-200c nanoparticles at 5 μg for 4 hrs and the cells are exposed to osteogenic medium. The dose of PEI-miR-200c is adjusted based on the dose dependent studies described herein. The transcript and protein level of β-catenin, Wnt-3A, Wnt-7A, Smad 1/5/8 is measured using real-time PCR and western blot after 1 and 7 days, respectively. These signal pathways have been demonstrated to actively interact with BMPs in osteogenic differentiation and bone formation. In addition, RNA sequencing and bioinformatics analysis are used to understand other molecular function of miR-200c overexpression on osteogenic differentiation of human MSCs. For RNA-seq, 1 μg RNA and the TruSeq Stranded Total RNA Library Prep kit (Illumina) is used to perform reverse transcription with bar-coded primers, complementary DNA amplification, and 100×100 paired ended sequencing with Illumina HiSeq 2000. Quality control of the obtained reads and mapping to the human reference genome (GRCm38/mm10) is performed using the combination of the Galaxy (https://main.g2.bx.psu.edu/) web-based analysis suite and in-house Perl scripts. Cufflink tool set will be used to analyze mapped reads to identify significant changes in gene expression. The low expression transcripts (less than 10 reads in all samples) are filtered out, and P values are adjusted using a threshold for false discovery rate (FDR)≤0.001. Differentially expressed transcripts are identified using threshold of fold change≥2 and FDR≤0.001. The differentially expressed genes are further used for hierarchical clustering performed using Cluster 3.0. Java Treeview for visualization. Gene ontology category enrichment is assessed using GOrilla (http://cbl-gorilla.cs.technion.ac.il/). LC Sciences (Houston, Tex.) does some miR analyses using human and mouse microRNA Arrays and they provide in-depth analyses with statistical values and enhanced bioinformatics. Q-RT-PCR analysis for specific genes is compared with the RNA sequencing results. Amplified VPS29 and actin is used to normalize the values.

Determination of the Molecular Function of miR-200a Inhibition.

Understanding the function and mechanism(s) of miR-200a inhibition on osteogenic differentiation provides information to develop a novel approach to promote bone regeneration and improve the osteogenic effects mediated by miR-200c and BMPs by using miR inhibitors.

miR-200a is a member of an miR-200 family that actively participates in the regulation of EMT and metastasis. Cancer research has revealed that, miR-200a directly suppresses β-catenin/Wnt signaling by directly targeting the 3' UTR of the β-catenin transcript. This miR also suppresses the expression of TGF-β2/Smad pathways by targeting Smad-interacting proteins. Given that the pathways of β-catenin/Wnt and TGF-β2/Smad play critical roles in osteogenesis and bone formation, these reports strongly suggested that miR-200a may reduce osteogenesis and inhibit bone formation. miR-200a inhibits BMP-2-induced differentiation of mouse preosteoblasts by targeting Dlx-5, a co-activator of Cbfa-1 (Runx-2). The studies discussed below also observed that the overexpression of miR-200a effectively suppresses the osteogenic capacities of human preosteoblasts by down-regulating a number of osteogenic transcription factors. Local application of miR-200a shows to significantly delay osseous fusion of the posterior frontal (PF) suture during mouse development (discussed below). These data demonstrated that miR-200a acts to repress osteogenic differentiation and inhibit bone formation. Thus, by inhibiting miR-200a inhibitory effect mediated by endogenous miR-200a on osteogenesis is eliminated. This approach shows synergy in the function of miR-200c and BMPs on osteogenic differentiation and bone regeneration.

Figure 7A:
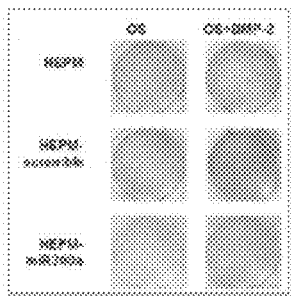
FIGS. 7A-7F. miR-200a represses the osteogenic differentiation of preosteoblasts in vitro.
Figure 7B:
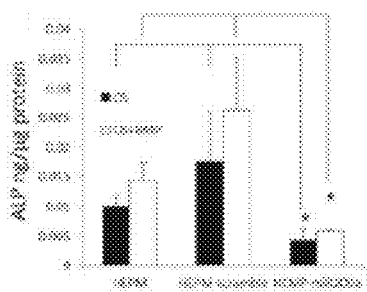
Figure 7C:
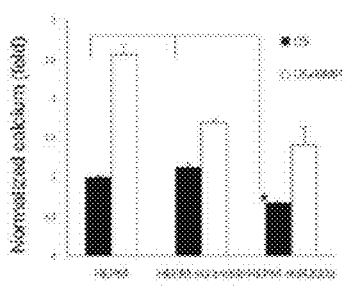
Figure 7D:
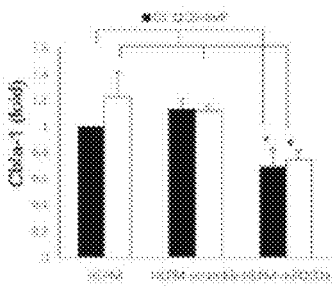
Figure 7E:
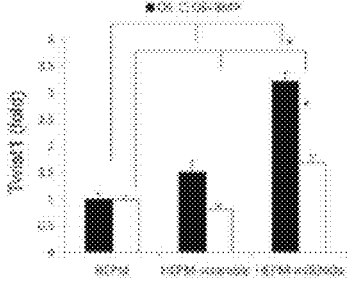
Figure 7F:
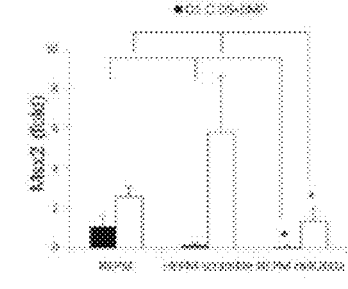
Figure 8A:
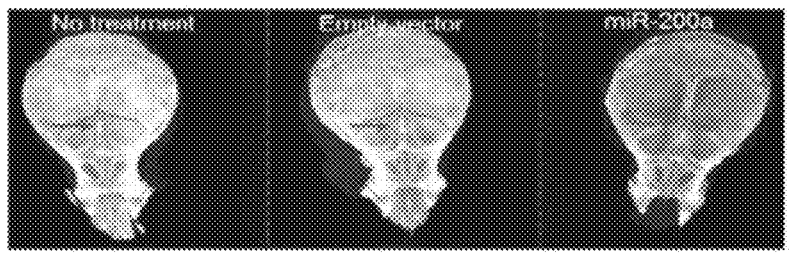
FIGS. 8A-8D. Effects of mir-200a on bone density and PF sutures in mouse skulls.
Figure 8B:
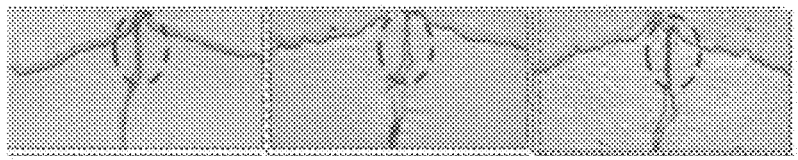
Figure 8C:
Figure 8D:

The current method to attenuate miR activity is the administration of anti-miR antisense oligonucleotides (AMO) into cells that compete for binding with endogenous targets. Although the ribonucleotides (oligos) are modified to increase their affinity towards miR sequences and protect the oligos from processing by cellular nucleases, a limitation of these miR inhibitors resides in their inability to be retained in the tissues after cell division and they must be reapplied to maintain their effectiveness. In order to address these limitations and promote long-term repression of specific miRs, attempts have been made to generate several plasmid and/or viral vectors expressing antagomirs, sponges, eraser and Tough Decoy (TuD) RNA. The inventors ahve recently developed a new plasmid-based miR inhibitory system (PMIS) based on hairpin structures that uniquely characterize miR transcripts (see, WO 2016/040347, which is incorporated by reference herein). The addition of short hairpin structure to antisense oligos greatly increased its inhibitory activity. These structures may coordinate physical interactions with proteins that bring the antisense oligo close to the miR and dramatically facilitate miR binding. The PMIS expresses anti-miR antisense oligos flanked by hairpin structures and contain features including AU rich flanking sequences and the plasmid may be transiently or constitutively expressed depending on the vector or integration. It has been demonstrated that the PMIS effectively and specifically knocks down specific miRs in cells based on the anti-miR antisense sequence.

miR-200a inhibits osteogenic differentiation of human preosteoblasts and osseous fusion of cranial suture of mouse. miR-200a was transfected into HEPM cells using a lentiviral vector. The preosteoblasts with miR-200a expression were cultured in osteogenic differentiation medium up to 2 weeks. The biomarkers of osteogenic differentiation, including ALP and calcium content, were significantly reduced in the cells with miR-200a overexpression, compared to control cells, even when the cells were cultured with BMP-2. Cbfa-1 mRNA was down-regulated approximately 2-fold (FIG. 7D), Twist1 was up-regulated 3-fold (FIG. 7E), and Msx2 was down-regulated 15-fold (FIG. 7F) in the cells with miR-200a overexpression. PF suture of the mouse is the only cranial structure in which anterior to posterior fusion occurs as early as postnatal day 15. Rapid and robust bone regeneration occur at this suture site in immature mice. The 100 µl lentivirus carrying miR-200a or the empty virus $10 \times 10^6$ (TU/ml) were injected subcutaneously at a position superficial to the PF suture weekly, starting at postnatal day 8. At postnatal day 30, the radiopacity of top of skulls of mice measured using µCT was lower in the animals receiving miR-200a than in either control (untreated and injected with empty vector) (FIG. 8A). While the PF sutures in both controls were nearly closed, those in mice receiving miR-200a injection remained open (FIG. 8B-C). FIG. 8D shows microphotographs of the histological cross-sections of PF sutures at a distance of approximately 0.5 mm from the bregma. Bony ridges had formed across the PF sutures in both controls, however, fibrous tissues still separated the bones in the mice injected with miR-200a. Quantitatively, µCT-based analysis of the radiodensity of the top of skulls of the mice receiving miR-200a (1420±76 HU) revealed a statistically significant reduction relative to controls (2112±65 and 2023±107 HU, respectively). The average "open length" of the PF suture in mice receiving miR-200a (0.94±0.1 mm) was about twice that in mice injected with empty vector and no treatment (n=5 *: p<0.05).

Figure 9:
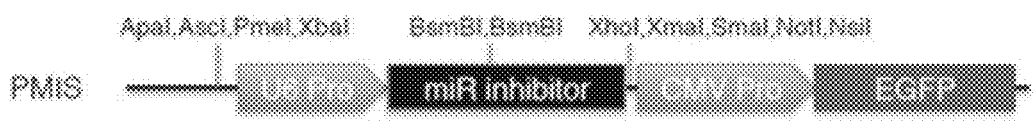
FIG. 9. The structure of the vector construct used to transduce cells.

Construction of PMIS-200a. To construct a miR inhibitor for miR-200a (PMIS-200a), a miR-200a binding site is annealed and ligated with a central bulge flanked by different sequences into pLL3.7 vector (Addgene) that is digested with HpaI and XhoI. To construct the miR inhibitor clone vector (PMIS-Vector), the miR-200a binding site is replaced with two BsmBI sites in the most effective inhibitor design. AscI and PmeI sites are inserted between ApaI and XbaI sites before the U6 promoter. A SmaI site is inserted before XhoI after the polIII terminator. This vector is termed PMIS-Empty Vector for plasmid based miR inhibitor system. After digestion by BsmBI, pPMIS-Vector is used to clone different miR inhibitors into it after annealing and ligating different miR binding sites with a central bulge (FIG. 9).

Biocompatibility and transfection efficiency of PEI-PMIS-200a nanoplexes: To test cytotoxicity, human bone marrow Mesenchymal stem cells (MSCs) are seeded at 10,000 cells/per well in a 96-well plate and treated with PEI-PMIS-200a nanoplexes at different N/P ratios.

Untreated cells act as controls, while cells treated with high dose PEI are used as a positive control to induce cytotoxicity. The same amount of PEI-PMIS-EV is also be included as a control. The cytotoxicity of PEI-miR-200c nanoplexes are determined using MTT assay after 4 and 24 hrs. To test transfection efficiency, human MSCs are seeded at $10^5$ cells/per well in a 6-well plate and treated with 1 µg of PEI-PMIS-200a nanoplexes with different N/P ratios. The expression of PMIS-200a and miR-200a is determined by real-time PCR after 48 hrs.

Osteogenic differentiation of human MSCs improved by PMIS-200a: Human bone marrow MSCs in a 6-well plate is treated with PEI alone, PMIS-200a alone, PMIS-EV alone, PEI-PMIS-200a nanoplexes, and PEI-PMIS-EV nanoplexes at 1, 2, 5, 10 µg at a N/P ratio of 10. The N/P ratio of PEI-PMIS-200a is adjusted based on the studies discussed herein. A commercially available miR-200a inhibitor is used as a control (Labome). The cells then are cultured in osteogenic medium consisting of DMEM medium supplemented with ascorbic acid and glycerophosphate, and the biomarkers of osteogenic differentiation are analyzed as described herein. In addition, Dlx-5 is measured.

Synergistic effects of PMIS-200a on the osteogenesis induced by miR-200c and rhBMP-2: Human bone marrow MSCs in a 6-well plate are treated with different combinations of PMIS-200a with miR-200c and rhBMP-2. PMIS-200a and miR-200c are incorporated into PEI nanoplexes at a N/P ratio of 10. rhBMP-2, PEI-PMIS-200a, and PEI-miR-200c at 1 µg/per well are used, respectively. PEI-empty vector and PEI-PMIS-EV serve as controls. The N/P ratio and doses of PEI-miR-200c and rhBMP-2 are adjusted based on the studies as described herein. The cells then are differentiated and the biomarkers of osteogenic differentiation are analyzed as described herein.

Molecular function of PMIS-200a in human MSCs: The function of PMIS-200a in BMP-associated signaling pathways during osteogenic differentiation is evaluated. MSCs are treated with PEI-PMIS-200a nanoparticles at 5 µg for 4 hrs and the cells are exposed to osteogenic medium. The dose of PEI-PMIS-200a is adjusted based on the dose dependent studies described herein. These BMP-associated signal pathways are measured as described herein. In addition, RNA sequencing and bioinformatics analysis is used to understand other molecular function of miR-200a inhibitors on osteogenic differentiation of human MSCs as described herein.

Development of a miR-based Approach for Oral and Craniofacial Bone Regeneration.

Significant bone regeneration induced by miR-200c and miR-200a inhibitors in periodontal and calvarial defects of rat models establish proof of concept for using a miR modulation to restore oral and craniofacial bone defects.

Calvarial bone defects in a rat model have been extensively used to evaluate the efficacy of synthetic materials on bone formation in vivo. This animal model is used to determine the efficacy of PEI nanoplexes containing miR-200c and miR-200a inhibitors on bone regeneration in vivo. In this model a collagen sponge is used as a scaffold to carry and release nanoplexes. It has been previously shown that PEI-pDNA (encoding for platelet derived growth factor-B (PDGF-B)) nanoplexes incorporated in collagen scaffold recruited significantly higher number of MSCs. The same delivery system can induce a significantly higher bone regeneration in a 5-mm calvarial defect in rats. The studies described herein also show that miR-200c at 10 µg/per defect loaded in collagen sponges improves bone formation in rat calvarial defects. By employing PEI nanoparticles to improve transfection efficiency, the efficacy of miR-200c and its ability on in vivo bone regeneration is significantly improved. In addition, by eliminating inhibitory effect of miR-200a using PMIS-200a bone formation is promoted in vivo.

Figure 10A:
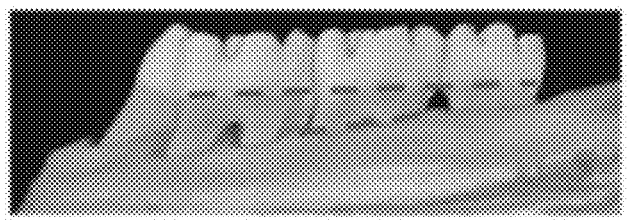
FIGS. 10A-10B. Representative μCT scans showing alveolar bone defects induced by local LPS injection at palatal gingiva around $2^{nd}$ maxillary molar after 4 weeks.
Figure 10B:
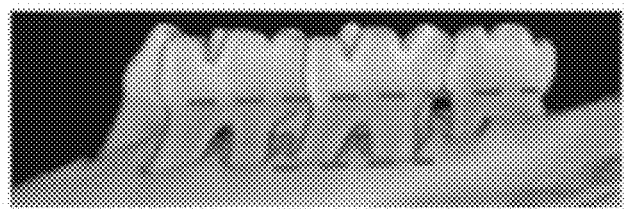

A rat model of periodontitis-induced bone defects is used to test the capacity of local injection of plasmid miR-200c to restore periodontal alveolar bone defects. miR-200c represses multiple proinflammatory cytokines by targeting their 3'UTRs and NF-kB. These proinflammatory factors impair bone formation by reducing differentiation of osteoblasts and their progenitor cells. Thus, miR-200c effectively arrests periodontitis and restores periodontal bone defect by reducing proinflammatory factors and increasing osteogenic differentiation. Local injection of allogeneic MSCs at periodontitis-induced bone defects around maxilla molars can regenerate bone and restore the defects. Studies described herein showed that direct injection of lipopolysaccharide (LPS) 10µg in 10µl PBS at palatal gingiva around the 2nd maxillary molar of rats twice every week will cause periodontal defects after 4 weeks (FIGS. 10A-10B). This model is used to test whether a local application of PEI-miR-200c released from biodegradable PLGA nanoparticles restores periodontal bone defects. The function of PEI-PMIS-200a to improve bone regeneration induced by miR-200c is tested in this model. PLGA nanoparticles have been developed that can effectively sustain the release of PEI-pDNA nanoplexes up to 35days. Also, PLGA-PEI nanoparticles incorporating miR-200a have been developed. By this delivery system, plasmid miRs was successfully delivered into human preosteoblasts and transfected cells in vitro (described below).

Plasmid miR-200c increases bone formation in rat calvarial defects. Fisher 344 rats were purchased from Harlan Laboratories. After the animals were anesthetized, two critical-sized (5 mm diameter) and full-thickness defects were generated on the parietal bone, on both sides of the sagittal suture of each rat. The four treatment groups including: 1) empty defect; 2) collagen scaffold; 3) plasmid miR-200c (10 µg/per defect); and 4) plasmid empty vector (10 µg/per defect) were randomly implanted into the defects. Rats were euthanized after 4 weeks. The µCT scans revealed increased quantities of mineralized bone matrix in the defects treated with collagen scaffolds containing miR-200c, compared to other treatment groups (FIG. 11A). The amount of bone tissue regenerated was quantified by analyzing the mineralized bone volume as a fraction of the total tissue volume of interest (BV/TV) and connectivity density of the regenerated bone. The BV/TV is more than 2-fold higher in defects treated with miR-200c, when compared to the controls (FIG. 11B).

PLGA-PEI nanoparticles transfect miRs into human preosteoblasts. Plasmid miR-200a was incorporated into PEI to form nanoplexes at an N/P ratio of 10. The complexes were subsequently incorporated into the PLGA (50:50, ester end) to make PLGA nanoparticles using double emulsion. The characteristics of the nanoparticles were analyzed. The average size of nano-particles was 750 nm. The surface charge of complex-loaded nanoparticles was −6 mV (FIG. 12A). The amount of plasmid miR-200a loaded in PLGA nanoparticles was 1.2 µg pDNA/mg nanoparticles, which was determined by a spectrophotometer (NanoDrop 2000 UV-Vis). In order to test the transfection of miR-200a, 1 mg miR-200a or scrambled miR-loaded PLGA-PEI nanoparticles were added into the medium of cultured HEPM cells. The medium was exchanged the next day to remove extra particles. On Day 3, overexpression of miR-200a in cells treated with miR-200a-loaded nanoparticles was confirmed using real-time PCR, while no expression of miR-200a was detected in cells treated with scrambled miRs (FIG. 12B).

The in vivo efficacy of PEI-miR-200c and PEI-PMIS-200a on calvarial bone regeneration: PEI-miR-200c and PEI-PMIS-200a nanoplexes at an N/P ratio of 10 is synthesized. The nanoplexes are then injected into a collagen sponge (8 mm-in-diameter and 2 mm thickness) and freeze-dried. A total of 210 twelve-week old male Fisher 344 rats are purchased. Under general anesthesia, a single circular defect of 8 mm in diameter is created using a trephine bur under saline irrigation without damaging the dura mater. The animals are randomly assigned to one of 14 groups (See table 1). Collage sponge is used as a scaffold. Animals are sacrificed after 1, 4, and 8 weeks. The samples from week 1 are used to determine uptake efficiency of PEI-miR-200c and PEI-PMIS-200a nanoplexes by analyzing miR-200c, miR-200a, and PMIS-200a expression using real-time PCR. The sample size per group will be 3 for this time point. The samples from week 4 and 8 are harvested for image and histological analyses. The sample size per group will be 6.

TABLE 1

Treatment groups for in vivo regenerative studies of miR-200c and PMIS-200a

| Group | Description |
|---|---|
| 1 | Empty defect |
| 2 | collagen scaffold |
| 3 | Empty vector (10 J · lg/defect) |
| 4 | miR-200c (1 µg/defect) |
| 5 | miR-200c (10 µg/defect) |
| 6 | PMIS-empty vector (10 µg/defect) |
| 7 | PMIS-200a (1 µg/defect) |
| 8 | PMIS-200a (10 µg/defect) |
| 9 | PEI-miR-200c (1 µg/defect) |
| 10 | PEI-miR-200c (10 µg/defect) |
| 11 | PEI-empty vector (10 µg/defect) |
| 12 | PEI-PMIS-200a (1 µg/defect) |
| 13 | PEI-PMIS-200a (10 µg/defect) |
| 14 | PEI-PMIS-empty vector (10 µg/detect) |

Effect of miR-200c and PMIS-200a to enhance bone regeneration of rhBMP-2: A total of 48 Fisher 344 rats are used and the calvarial defects are prepared as described herein. rhBMP-2 alone at a higher concentration (2.5 µg/defect) has been demonstrated to restore the defects. Collage sponge is used as a scaffold. Table 2 summarizes the treatment groups with different combinations of miR-200c, PMIS-200a, and rhBMP-2. The doses of rhBMP-2 are adjusted based on a pilot study with small number of rats. The samples from week 4 are harvested for analyses to determine the synergistic effects of combinations of miR-200c, PMIS-200a and rhBMP-2 on bone regeneration.

TABLE 2

Treatment groups for synergistic effect of miR-200c, PMIS-200a, and BMP-2

| Group | Description |
|---|---|
| 1 | BMP-2 (0.1 µg) |
| 2 | BMP-2 (2.5 µg) |
| 3 | PEI-miR-200c (1 µg) + PMIS-empty vector (1 µg) |
| 4 | PEI-empty vector + PEI-PMIS-200a (1 µg) |
| 5 | PEI-miR-200c (1 µg) + PEI-PMIS-200a (1 µg) |
| 6 | BMP-2 (0.1 µg) + PEI-miR-200c (1 µg) |
| 7 | BMP-2 (0.1 µg) + PEI-PMIS-200a (1 µg) |
| 8 | BMP-2 (0.1 µg) + PEI-miR-200c (1 µg) + PEI-miR-200a (1 µg) |

Injectable nanoparticles releasing PEI-miR-200c and PEI-PMIS-200a to restore periodontal bone defects. Plasmid miR-200c and PMIS-200a are incorporated into PEI to form nanoplexes at an N/P ratio of 10, respectively. The complexes are subsequently incorporated into the PLGA (50:50, ester end) to make PLGA nanoparticles using double emulsion. The characteristics of the nanoparticles are analyzed. The amount of pDNA loaded in PLGA nanoparticles is determined by a spectrophotometer (NanoDrop 2000 UV-Vis). A total of 38 Fisher 344 rats are used to create 76 periodontal defects around the $2^{nd}$ maxillary molar as described (FIGS. 10A-10B). Two rats are euthanized after 4 weeks and the periodontal defects are confirmed using µCT and histomorphological analysis. The 72 defects subsequently are randomly assigned to 6 groups: 1) no treatment; 2) PLGA nanoparticles containing empty vector; 3) PLGA nanoparticles containing PEI-miR-200c (10µg/per defect); 4) PLGA nanoparticles containing PMIS-empty vector; 5) PLGA nanoparticles containing PEI-PMIS-200a (10µg/per defect); and 6) PLGA nanoparticles containing miR-200c and PMIS-200a (10µg/per defect). Nanoparticles carrying different treatments are suspended in 0.1ml type I collagen gel and injected at 3 sites of $2^{nd}$ molar (the mesial and distal sides of the molar, and the middle of the molar). The doses of miR-200c and PMIS-200a are adjusted as needed. The needle is inserted from the mucosa to the bone surface, and the nanoparticles suspended in saline are injected after significant resistance is encountered. Normal rats without any treatment serve as positive controls. Animals are sacrificed after 1, 4, and 8 weeks. The samples from week 1 are used to determine uptake efficiency of PEI-miR-200c and PEI-PMIS-200a nanoplexes by analyzing miR-200c, miR-200a, and PMIS-200a expression using real-time PCR. Samples from week 4 and 8 are used for image and histological analyses.

Assessment of bone regeneration for calvarial defects. µCT and histomorphometric methods are used to quantitatively analyze calvarial bone regeneration after 4 and 8. µCT imaging is performed on the specimens using a cone-beam µCT system (µCT40, Scanco Medical AG). Specimens are scanned in 70% ethanol at 55 kVp and 145 µA with a voxel size of 10 µm and an integration time of 300 ms. Analysis is performed using a constant 8 mm diameter circular region of interest that is placed in the center of the machined defect and spanned a total of 50 reconstructed slices using the manufacturer's software. Bone volume per total volume and connectivity density in the bone defect is obtained. After µCT measurement, the bone samples are decalcified and introduced into a paraffin processor for paraffin processing. Histological analysis is performed on the 5 µm sections in the central portion of the wound. The sections are stained with hematoxylin and eosin and immunohistochemically stained for fibronectin, collagen I, collagen V, osteocalcin, and osteonectin.

Assessment of bone regeneration for periodontal alveolar defects. After µCT imaging is performed on the specimens as described herein, analysis is performed using a constant 3.5 mm diameter circular region of interest that is placed in the center of the machined defect and spanned a total of 50 reconstructed slices. µCT data is acquired and reconstructed using the manufacturer's software. This enables the observation of the morphology around the tooth and dental alveolar bone in all dimensions, including the cemento-enamel junction (CEJ), root surface and dental alveolar crest, as well as the relationships among these areas. µCT with reconstructed 3D images are used to assess the distance between the CEJ and the coronal level of the alveolar bone crests (the μCT bone levels) at 4 sites, including the mesiobuccal and distobuccal sites, and the mesiopalatal and distopalatal sites of the maxillary 2nd molars. For histomorphometric analysis, the specimens are cut into 10 μm sections sagittally and stained with hematoxylin and eosin (HE) and tartrate-resistant acid phosphatase (TRAP) staining. The images are captured with a digital camera coupled with the microscope and connected to a computer, and are analyzed using Image J image-analysis software. On the mesial surfaces of the 2nd molars receiving different treatments, the following histometric measurements are performed: the distance of the CEJ to the coronal level of epithelial cells (attachment loss); the distance of the CEJ to the alveolar bone crest; the distance of the apical level of epithelial cells to the alveolar bone crest; and the area of inflammatory cell-infiltrated connective tissue.

Statistical Analysis: The primary outcomes of the experiments described above are the percentage of new bone volume derived from μCT analysis and new bone area derived from histomorphometric analysis. Two-way analysis of variance (ANOVA) is used to assess effects of treatment and time, including possible interactions, using a Type I error level of 0.05. Pairwise comparisons among treatments within a specific time are assessed using the Holm modification of the Bonferroni adjustment for multiple comparisons in conjunction with an overall Type I error level of 0.05. In the presence of interaction, pairwise comparisons are made a time point.

EXAMPLE 2

The present example evaluates an alternate, less invasive bioregenerative strategy to rescue or prevent the osseous fusion of sutures and ultimately to ameliorate the outcome of craniosynostosis treatment. An effective protocol using RNA interference to block signaling pathways of osteogenic differentiation induced by FGF-2, TGF-β1, 2, and/or BMP-2, and by doing so, prevents the effects of these osteo-inductive cytokines on suture fusions. The present data demonstrate that: 1) microRNAs (miRNAs) function in transcriptional and post-transcriptional regulation of gene expression and can be potentially used to silence gene expression via translational repression or target degradation; 2) miRNA-200 family effectively down-regulate the expression of β-catenin, which is a key factor in the signaling pathways of FGF/BMP/Wnt mediated osteogenic differentiation, and these miRNAs may also suppress Smad expression, which mediate TGF-β/BMP-induced osteogenesis; 3) overexpression of miR-200a inhibits BMP-2-induced preosteoblast differentiation and repressed TGF-β2 expression; 4) overexpression of miR-200a and 200c effectively down-regulated the expression of transcription factors of osteoblast differentiation and reduced osteogenic differentiation of preosteoblasts.

One in every ~2,500 newborns suffers from craniosynostosis, a congenital disorder characterized by bony fusion of cranial sutures before completion of brain and calvarial growth. These children may develop visible craniofacial disfigurations. Children suffering from craniosynostosis may develop severe neurological disorders such as mental retardation, blindness and seizure that result from increasing intracranial pressure. Craniofacial surgery is the primary choice for correcting visible craniofacial disfigurations and relieving abnormally high intracranial pressure. Surgeons typically perform craniotomy in early childhood by dissecting out fused sutures and leaving gaps of empirical size between involved calvarial bones, aiming that the surgically created gaps may accommodate both brain growth and calvarial bone growth to compensate for craniofacial disfigurations. The surgical approach for craniosynostosis unavoidably causes many severe problems such as extreme amount of blood loss (250 to 1500 ml/per operation) and surgical trauma. Although a minimally invasive approach using endoscopy has been developed, this option is only available to patients who are less than 3-6 months old. Due to about 50% higher osteogenic potential of calvarial bone in these patients compared to normal subjects, about 35% of patients need multiple surgeries to remove re-synostosed sutures. Several early approaches were attempted to decrease the osteogenic potential of dura mater or prevention of bone healing using chemical agents and physical blocks. However, scientific proof of the efficacy of these procedures is questionable, and side effects involving damage of the cerebral cortex have been reported.

Approximately 50% of patients have been found to have genetically based familial craniosynostosis syndromes. Mutations of Msx2, TGF-β, FGFR, TWIST, and Nell1 genes are linked to craniosynostosis. These mutations have been demonstrated to lead to excessive signaling of a number of osteo-inductive cytokines, including FGF-2, BMP-2, 4, 7, and TGF-β1, 2, which subsequently promote osteoblast proliferation, differentiation and bone matrix formation.

Determination of the Suppressive Effects of miRNAs on FGF/TGF-β/BMP-induced Osteogenic Differentiation.

FGF-2, TGF-β1, 2, and BMP-2 have been demonstrated to actively participate in osseous fusion of cranial sutures. FIG. 13 summarizes the potential signaling pathways of these cytokines and their crosstalk in the regulation of the proliferation and osteogenic differentiation of osteoblasts and their progenitor cells. Briefly, FGF-2 increases proliferation of osteoblasts and their progenitor cells and promotes osteoblast survival via the pathways of mitogen-activated protein kinase (MAP K), extracellular signal-regulated kinases (ERK)1, 2, and c-Jun N-terminal kinases (INK). FGF-2 also promotes osteogenic differentiation by crosstalk with TGF-β/BMPs through β-catenin accumulation. In addition, ERKJ/2 signaling driven by FGF-2 has been demonstrated to participate in the regulation of TGF-β2 in suture fusion. TGF-βs/BMPs signaling in inducing osteogenic differentiation are mediated by Smad pathways, resulting in the up-regulation of the Smad4 gene. The Dlx5 gene, a transcription factor downstream of Smad4, has been demonstrated to accompany BMPs-induced osteogenic differentiation. In addition, BMPs interact with Wnt/β-catenin signaling to enhance their effects on osteogenic differentiation. These signaling pathways lead to the up-regulation of osteogenic transcription factors, including Runt-related transcription factor (Runx)2 and osterix (Osx), which subsequently differentiate MSCs (the progenitor cells of osteoblasts) and preosteoblasts into osteoblasts, thereby promoting bone formation. Therefore, by repressing the expression of these mediators and/or transcription factors in osteoblast progenitor cells, these cells may effectively be protected from the osteo-inductive signaling of FGF/TGF/BMP cytokines. The members within the miRNA 200 family have been demonstrated to effectively interfere with the signaling pathways of multiple osteogenic cytokines and participate in the regulation of osteogenic differentiation. These previous findings include: 1) miRNA 200s repress both TGF-β/BMP-induced effects in renal fibrosis and cancer developments by reducing the expression of multiple mediators that play actively roles in osteogenic signaling pathways of these cytokines. Specifically, miR-200a directly targets β-catenin mRNA, which contains a functionally conserved miR-200a-binding site in its 3' UTR, and suppresses β-catenin/Wnt signaling; 2) miR-200a and -200c may suppress Smad pathways by targeting smad-interacting proteins, and also represses the expression of TGF-β2; 3) overexpression of miR-200a has been demonstrated to inhibit BMP-2-induced osteogenic differentiation of preosteoblasts by targeting the expression of Dlx5.

As described below, the present studies have successfully infected miR-200a and 200c using lentiviral vectors into human embryonic palatal mesenchymal (HEPM) cells, a well-established preosteoblast cell line. Overexpression of miR-200a and 200c is shown to effectively reduce the expression of Runx2 and osteogenic biomarkers in HEPM cells. Thus, miR-200a and 200c suppresses osteo-inductive effects of FGF-2, TGF-βs, and BMPs by interfering with their signaling pathways.

miR-200a or 200c Inhibits Osteogenic Differentiation of Preosteoblasts.

The lentivirus containing plasmid miR-200a or 200c were produced by transfection of three plasmids, including psPAX2, pMD2G, and plasmid miR-200a or 200c into HEK 293T cells using a standard CaCl2 method. Briefly, 1.8 μg of psPAX2, 1.2 μg of pMD2G, and 4.2 μg of plasmid miR-200a or 200c were mixed with 14 μl of 2M CaCl2, 2 μl of 10 mg/ml polybrene in FIBS buffer (pH 7.05) to constitute the transfection solution. The transfection solution was dropped into culture plates containing 20-30% confluent 293T cells and exchanged using fresh medium after 24 hrs. The supernatant containing lentivirus of plasmid miR-200a or 200c was then harvested after 72 hrs and filtered through a 0.45 μm sterile syringe. In order to transduce the lentivirus containing plasmid miR-200a or 200c into HEPM cells, about $100 \times 10^6$ (TU/ml) lentivirus were added to HEPM cell suspension and incubated overnight. The medium containing the same amount of lentivirus carrying miR-200a or 200c was exchanged every day up to 3 days. FIG. 14A shows the microphotographs of HEPM cells with green fluorescent protein (GFP) staining after infection of miR-200a, 200c, and a scrambled negative control miRNA under fluorescent microscopy. About 70% of cells are GFP positive measured by FACscan flow cytometer (FIG. 14A). The overexpression of miR-200a or 200c in HEPM cells with different treatment was confirmed using real-time PCR (FIG. 14B). These cells were subsequently cultured in complete DMEM or osteogenic medium consisting of complete DMEM supplemented with 10 mM β-glycerophosphate and 0.05 mM ascorbic acid-2-phosphate up to 2 weeks. The gene expression of Runx2, a transcription factor of osteoblast differentiation, and alkaline phosphatase (ALP), a biomarker of osteogenic differentiation, were reduced in HEPM cells after infection of miR-200a or 200c (FIG. 14C). The calcium content in infected HEPM cells cultured in osteogenic medium was reduced (FIG. 14D).

FIGS. 15A-15D illustrate the experimental procedure designed to understand the repressive effects and potential underlying mechanism(s) of miR-200a and/or 200c on FGF/TGF/BMPs-induced osteogenic differentiation. HEPM cells and bone marrow MSCs are purchased commercially (ATCC and Stemcell). The cells are infected with different miRNAs as listed in FIG. 15B using lentiviral vectors as described herein. A scramble miRNA serves as a control. The infection of miRNAs are confirmed by real-time PCR and flow cytometry. GFP-positive cells sorted by FACsan are placed in a 6-well plate at $10^4$ cells/per well and exposed to osteogenic medium as described herein. FGF-2 (2.5 ng/ml), TGF-β1(0.1 μg/ml), TGF-β2(0.1 μg/ml), and BMP-2 (50 ng/ml) are added to the medium with different combinations as listed in FIG. 15C. Previously published studies have demonstrated that these concentrations of cytokines effectively enhance osteogenic differentiation of preosteoblasts and/or human MSCs. In addition, combining FGF-2 with BMP-2 or TGF-βs has been demonstrated to synergistically promote their effects on osteogenic differentiation. After 1, 4, 7, 14, and 28 days, the cells are collected and measured for transduction mediators, transcription factors, and epigenetic biomarkers of osteogenic differentiation as listed in FIG. 15D. The mediators and osteogenic transcription factors are quantitatively measured using both real-time PCR and western blot. DNA quantification and a 5-Bromo-2'-deoxy-uridine (BrdU) assay are used to measure the proliferation rate of osteoblast progenitor cells. Osteogenic biomarkers, including ALP, osteopontin (OPN), osteocalcin (OCN), bone sialoprotein (BSP), and calcium content, are measured using real-time PCR, immunohistochemical staining, and ELISA methods. All samples will be measured in triplicate.

Determine Inhibitory Effects of miRNAs on Cranial Sutural Fusion.

MiR-200a postpones osseous fusion of cranial sutures by repressing osteogenic differentiation and bone formation induced by FGF/TGF/BMP cytokines.

Mutations of Msx2, FGFR, TWIST, and Nell1 genes have been found in patients who have familial craniosynostosis syndromes. These mutations lead to excessive signaling of a number of osteogenic cytokines, including FGF-2, BMP-2, 4, 7, and TGF-β1, 2, which enhance osteogenic differentiation of suture cells and accelerate osseous fusions. Patients with these familial craniosynostosis syndromes have been demonstrated to display higher rates of re-synostosis necessitating multiple surgeries. As mentioned above, miR-200a has been demonstrated to effectively inhibit the expression of transduction mediators that participate in osteogenic signaling of TGF-β/BMPs.

The posterior frontal (PF) suture in rodents, analogous to the human metopic suture, fuses during early development whereas most the sutures in the rodent skull remain patent to allow for continued cranial expansion. Cytokines, including FGF-2, TGF-β1, 2, and BMP-2, 4, 7, have been identified at the underlying dura mater of posterior frontal (PF) sutures. These osteo-inductive cytokines are considered to coordinately contribute to osseous fusion of PF sutures. Supplementation of FGF-2 or TGF-β2 has also been shown to accelerate the fusion of PF sutures in organ culture. Thus, this model has been frequently used to study the roles of both suture fusion in craniofacial development and the regulation of cytokines in suture fusions. In this study, this model is used to investigate the inhibitory effects of miR-200a on osseous fusion of cranial sutures that are dominated by excessive signaling of osteo-inductive cytokines. Since lentiviral vectors have been reported to be used to infect plasmid miRNAs into multiple tissue types in organ culture, in this study we will use this vector to infect plasmid miR-200a into sutural tissues.

Calvarial rudiments are collected from male CD-1 mice (Charles River) that are sacrificed by carbon dioxide asphyxiation on postnatal day 5. Calvaria with intact dura mater are placed in, with the dura mater side down, 24-well plates that are covered with DMEM medium supplemented with 100 mg/ml ascorbic acid. An optimal concentration of lentiviral vectors of plasmid miR-200a or the same concentration of scramble miRNA, as well as the cytokines as listed in Table 1, is added into the culture medium. The organ culture media is exchanged every 2 days up to 30 days. Different concentrations of lentiviral vectors carrying plasmid miR-200a are added to organ culture of calvaria. After 1, 4, and 7 days, real-time PCR and histological analysis are used to determine the overexpression of miR-200a and GFP-positive staining in PF suture tissues. After 5, 15, and 30 days of organ culture, calvaria with different treatments listed in Table 3 are collected and analyzed for suture patency and level of apoptosis. The expression of transduction mediators that function in FGF/TGF/BMP signaling pathways and osteogenic transcription factors are evaluated.

TABLE 3

| Group | Cytokines | miR-200a | Scramble miR |
|---|---|---|---|
| 1 | NA | — | 6 |
| 2 | NA | 6 | — |
| 3 | FGF-2 (50 ng/ml) | — | 6 |
| 4 | FGF-2 (50 ng/ml) | 6 | — |
| 5 | TGF-2 (3 ng/ml) | — | 6 |
| 6 | TGF-2 (3 ng/ml) | 6 | — |
| 7 | FGF-2/TGF-2 | — | 6 |
| 8 | FGF-2/TGF-2 | 6 | — |

PF sutures are dissected from the calviara as indicated in FIGS. 16A-B and cut in half at a dashed line as in FIG. 16A. Fibrotic tissues are dissected carefully from half of each suture and total mRNA, DNA, and protein are extracted from the fibrotic tissues using commercially available kits. Real-time PCR is used to determine the gene expression of transduction mediators in osteogenic signal pathways, including Smad4, Dlx5, Elk1/2, and β-catenin, and osteogenic transcription factors, including Runx2 and Osx. The protein levels of these mediators and transcription factors are measured using western blot. The cytoplasmic histone-associated DNA fragments in the suture homogenates are evaluated using a Cell Death Detection ELISA kit to determine the extent of apoptosis. Histomorphometric analysis is used to determine suture patency. Briefly, half of each suture is fixed in 4% paraformaldehyde and decalcified in formic acid and sodium citrate. Control and experimental tissues are mounted in the same paraffin blocks and the coronal suture are placed at the base of the paraffin form to ensure consistent orientation of all tissue samples. Suture samples are then sectioned in 6-μm sections beginning at 100-μm intervals from the coronal suture (FIG. 16A). The sections are stained with hematoxylin and eosin stains. All sections are subsequently imaged with a digital camera and analyzed using Image J 1.36 software. All samples are analyzed in an endocranial-ectocranial dimension to determine the extent of cranial suture bridging.

Data are collected beginning posteriorly at the coronal suture and continued to a point 2000 μm anteriorly. This measuring technique is illustrated in FIG. 16B and each condition and time point is duplicated in six independent experiments. The most inferior point of the suture ridge in the sutural gap is labeled point A. Then a line is drawn from point A to a point where it intersects a line connecting the most superior points of the bony fronts. This intersection is labeled point B. The distance from point A to point B is defined as the sutural height. From point A, a second line will be drawn to the most superior point of bony bridging, labeled point C. The distance from point A to point C will be defined as the bridging height. Percentage bridging is calculated for each section by dividing the bridging height by the sutural height.

Rescue Sutural Osseous Fusion Using miRNAs.

Local application of miR-200a is used to prevent osseous fusion of cranial sutures for craniosynostosis treatment. While the etiopathogenic mechanisms of sporadic craniosynostosis cases are still elusive, familial mutations have been demonstrated to lead to increasing multiple osteo-inductive cytokines, including FGF-2, TGF-1, 2, and BMP-2, 4, 7. The excessive signaling of these cytokines results in 50% higher osteogenic potentials of calvarial bone in these patients and greatly affects the apoptosis of suture cells. Thus, cytokine-targeted are used as an alternative for craniosynostosis treatment. However, since the suture biology and etiopathogenesis of craniosynostosis involve multiple coordinated osteogenic cytokines, single cytokine-targeted approaches may not be sufficient to inhibit these excessive osteo-inductive signals. As mentioned above, miR-200a may repress a number of osteogenic signaling pathways induced by multiple cytokines, including FGF-2, TGF-β1 and BMP-2. Overexpression of miR-200a has also been demonstrated to inhibit the synthesis of TGF-β2, which is a key osteogenic cytokine participating in suture fusion. In addition, overexpression of miR-200a inhibits the effects mediated by BMP-2 on the differentiation of preosteoblasts. This evidence strongly indicates that miR-200a is more efficient in inhibiting osseous fusion of cranial sutures than single cytokine-targeted approaches, which may potentially be developed for craniosynostosis treatment. In this study, a rat PF suture model is used to prove the concept that local application of miR-200a will effectively rescue osseous fusion of cranial sutures.

Fifteen-day-old Sprague-Dawley rats are purchased (Charles River) and anesthetized with ketamine and Xylazine. Animals are randomly assigned to one of the different treatment groups: 1) negative control without any treatment; 2) empty collagen gel; 3) collagen gel containing $10 \times 10^6$ (TU/ml) lentivirus carrying plasmid miRNA-scrambled; 4) collagen gel containing $100 \times 10^6$ (TU/ml) lentivirus carrying scrambled miRNA; 5) collagen gel containing a low concentration of lentivirus with plasmid miR-200a ($10 \times 10^6$ TU/ml); and 6) collagen gel containing $100 \times 10^6$ (TU/ml) miR-200a lentivirus. Different concentrations of lentivirus carrying plasmid miR-200a are mixed with 0.1 mg/ml collagen gel. The mixture (100 μL) is injected subperiosteally with a 21-gauge needle located superficially to the PF sutures. This volume of collagen gel has been demonstrated to sufficiently cover 3 to 4 mm of the posterior frontal suture anterior to the coronal suture. After 10 and 20 days, animals are euthanized by $CO_2$ narcosis and calvariae are harvested. BrdU at 1.4 g/kg is injected intraperitoneally before sacrifice. After tissue collection, suture tissues for the molecular biological measurement and histomorphometrical analysis are processed as described below. The expression of miR-200a, transduction mediators of FGF/TGF/BMP pathways, and osteogenic transcription factors are quantitatively measured as described below. The suture patency is quantified as described below. A commercially available kit of BrdU staining is used to determine the proliferation of suture cells. Also the cytokines are evaluated, including FGF-2, BMP-2, 4, and TGF-1, 2, 3, within PF suture and underlined dura mater using immunohistomorphometric analyses.

EXAMPLE 3

In previous studies it was observed that miR-200c knockout mice exhibit tooth and bone defects development. miR-200c overexpression could significantly upregulate osteogenic biomarkers in human preosteoblasts and bone marrow MSCs (FIGS. 17A-17B). Recent studies have further demonstrated that plasmid miR-200c loaded in collagen sponges can significantly promote bone formation in calvarial defects of a rat model (PS-1). This evidence strongly indicates that miR-200c has a strong potential to become an osteo-inductive agent for clinical therapeutic purposes. However, the mechanism(s) by which miR-200c enhances osteogenesis is not yet known. Recent studies (PS-2) have observed that miR-200c overexpression down-regulated Sox2 and Klf4 in human bone marrow MSCs. Sox2 and Klf4 are key transcription factors in inducing iPSC cells, and play a critical function in the maintenance of cellular pluripotency in stem cells and multiple differentiation as well. They also participate in the regulation of Wnt pathway and potently inhibit osteogenic differentiation in human MSCs. MicroRNA target predication (Exqion) indicates that miR-200c may directly target 3 'UTR of Sox2 and Klf4. Studies (PS-3)have demonstrated that miR-200c could up-regulate activity of Wnt signaling; however, Sox-2 might repress it. Thus, it is likely that miR-200c up-regulates Wnt signaling by targeting Sox2 and Klf4.

Additionally, because the function of miRs is executed differently compared to other osteogenic factors in bone formation, it is necessary to understand the role of miR-200c transfection in its osteogenic capacity. This provides important information for developing an optimal gene delivery system to improve the effectiveness of miR-200c. Initial studies have shown that the expression level of miR-200c was in a dose-dependent manner while naked plasmid miR-200c was used in vitro (FIG. 18A). This provided the feasibility to correlate the biomarkers of osteogenic differentiation with the level of miR-200c transfection. Polyethylenimine (PEI) is a cationic polymer that is one of the most efficient non-viral vectors in vitro and in vivo. PEI is a water-soluble polymer in which the repeat unit of PEI is two carbon atoms followed by a nitrogen atom. Under physiological conditions, approximately 20% of the nitrogens are protonated. The positive charge of the PEI results in effective binding to the negatively charged plasmid miRs, and this condensation protects the plasmid from digestion in serum and as the nanoparticle complex enters cells. Once in the endosomal compartment, PEI can act as a buffer or "proton sponge" to induce osmotic swelling and cause release from the endosome. This is necessary to avoid degradation of the plasmid miR when the endosome fuses with the lysosome PEI nanoparticles as a non-viral gene delivery system could improve transfection efficiency of plasmid DNA. PEI can improve approximately 100 times transfection efficiency of miR-200c compared to naked plasmid DNA (FIG. 18B). However, the transfection efficiency using PEI is strongly correlated to its cytotoxicity. Previous studies have demonstrated to N/P ratios [the ratio of the total number of end amine groups (N) of PEI and the total number of DNA phosphate groups (P)] significantly influence the size, surface charge, transfection efficiency and cytotoxicity of PEI nanoplexes. Thus, by modulating the N/P ratio, we may develop an optimized PEI delivery system with a high transfection efficiency but with limited cytotoxicity.

Plasmid miR-200c improves bone formation in vivo. Calvarial defects of a SD rat model were used. After the animals were anesthetized, two 5 mm-diameter, full-thickness defects were generated on the parietal bone, on both sides of the sagittal suture of each rat. The treatment groups: 1) empty defect; 2) collagen scaffold; 3) plasmid miR-200c; and 4) plasmid empty vector (EV), at different doses, were randomly implanted into the defects. To determine the in vivo transfection of miR-200c, rats were euthanized after 1 week and the entire RNA were collected from the collagen sponges. It was observed that miR-200c was overexpressed in a dose-dependent manner and higher than controls (FIG. 19A). The μCT scans revealed increased quantities of mineralized bone matrix in the defects treated with collagen scaffolds containing miR-200c, compared to other treatment groups after 4 weeks (FIG. 19B). The amount of bone tissue regenerated was quantified by analyzing the mineralized bone volume as a fraction of the total tissue volume of interest (BV/TV) and connectivity density of the regenerated bone. The BV/TV in the defects treated with miR-200c at 10 μg/per defect (46.0±14.6, n=6) was approximately twofold higher in defects with untreated (22.7±6.5, n=3), empty sponges (25.9±9.1, n=3), and emptor vector control at 10 μg/per defect (24.2±6.0, n=3). Histological images of a cross-section of defects shows the bone defects and regenerated bone by miR-200c (FIG. 19C).

miR-200c inhibits Sox2 and Klf4. Primary human bone marrow MSCs cultured in 6-well plants were treated overnight with plasmid miR-200c (5ug/per well), or the same amount of empty vector. After 72 hours, the RNA was isolated from cells using the Qiagen miRNA easy kit, and cDNA from those RNAs was generated using Biorads PrimePCR cDNA kit, and the quality of the cDNA by qPCR was validated. Approximately fivefold higher expression of miR-200c was observed in the MSCs treated with miR-200c than the cells treated with empty vector (FIG. 20A). The Biorad PrimePCR assay system was first used to detect variations of Wnt and TGF/BMP signaling (Bio-Rad). Each plate was compared using Biorad CFX manager 3.1. The gene showing a twofold increase of reduction was subsequently tested and validated using real-time PCR. It was discovered that Sox2 and Klf4 are significantly reduced in the MSCs treated with miR-200c (FIG. 20A). MicroRNA target predication (Exqion) indicates that miR-200c may directly target 3 'UTR of Sox2 and Klf4 (FIG. 20B).

Figure 21:
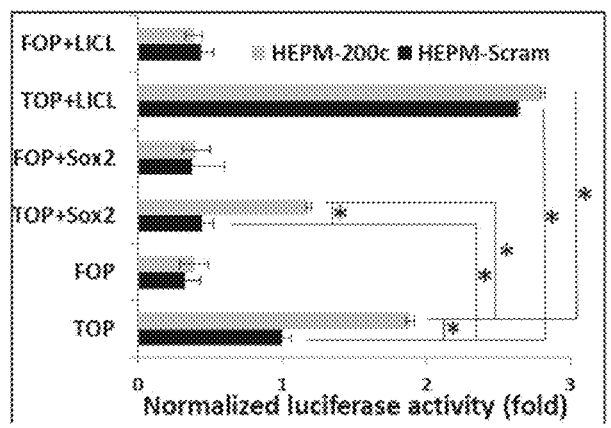
FIG. 21. The normalized relative Wnt signaling intensity (TOPflash) in HEPM cells with overexpression of miR-200c or scramble miRs after transfection with and without Sox2. N=3, *p:<0.05.

Wnt activity regulated by miR-200c and Sox2. HEPM cells (a human preosteoblast cell line) were used to test the regulation of miR-200c and Sox2 on Wnt signaling. Scrambled-miRs or miR-200c were transfected into HEPM cells using a lentiviral vector. The Wnt reporter gene (TOPflash), with or without Sox2 reporter, was further transfected into the HEPM cells with miR-200c and scrambled miRs. FOPflash was used as a negative control. This assay measures the activity of a luciferase reporter whose expression is under the control of the TCF/LEF promoter to provide an assessment of β-catenin or Wnt ligand-stimulated activation of TCF/LEF mediated transcription. Under the stimulation of LICL, an inhibitor of GSK3, TOP (Wnt signaling) was effectively activated in both HEPM with miR-200c and scrambled miRs. However, the cells with overexpression of miR-200c had significantly higher TOP than the cells with scrambled miRs. LICL has no function on FOPflash. Sox-2 reduced TOP in both cells with overexpression of miR-200c and scrambled miRs. However, the TOP in cells with miR-200c overexpression under Sox2 transfection was still higher than the cells with scrambled miRs (FIG. 21). This evidence indicates that miR-200c up-regulates Wnt signaling and the upregulation may be via Sox2 repression.

EXAMPLE 4 miR-200a suppresses β-catenin/Wnt signaling and TGF-β2/Smad pathways, which are the key factors in osteogenesis and bone formation. miR-200a also inhibits BMP-2-induced differentiation of mouse preosteoblasts by targeting Dlx-5, a co-activator of Runx2. Recent studies (PS-4) demonstrated that miR-200a overexpression down-regulates osteogenic differentiation in human preosteoblasts. miR- 200a may also down-regulate Pitx-2, a transcriptional factor that potentially up-regulates Wnt signaling and miR-200c expression (PS-4). These previous studies indicated that by eliminating the inhibitory effect of miR-200a we may effectively improve osteogenic differentiation and bone formation.

Figure 22A:
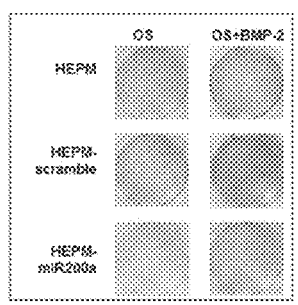
FIGS. 22A-22E. miR-200a represses the osteogenic differentiation and Pixt2.
Figure 22B:
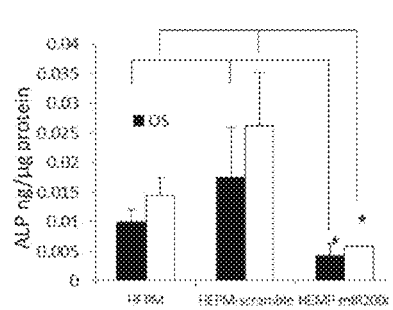
Figure 22C:
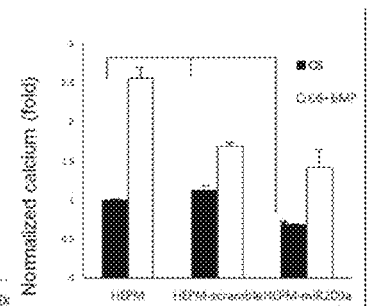
Figure 22D:
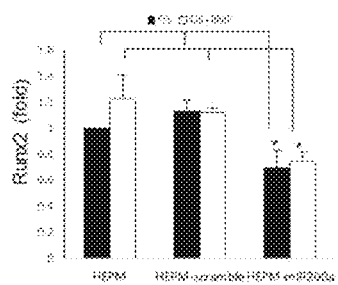
Figure 22E:
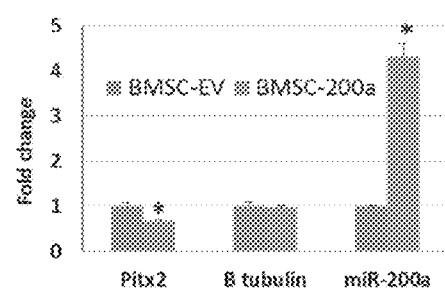

A novel PMIS was have developed to modulate miR-200a activity. PMIS modulates miR function by expressing a small non-coding RNA molecule that contains a specific antisense mature miR sequence. PMIS-200a specificity and efficiency has been validated in vitro. For example, PMIS-200a can inhibit both miR-200a and miR-141 as they share the same seed sequence. PMIS-200a has no inhibition effects on miR-200b and miR-200c. These results support the feasibility of using the PMIS inhibitor as a reagent to modulate miR-200a activity. Studies have shown that PMIS-200a can effectively be transfected into human bone marrow MSCs in a dose-dependent manner to significantly inhibit endogenous miR-200a (PS-5). Furthermore, our preliminary studies have shown that PMIS-200a loaded in a collagen sponge could significantly improve bone formation (PS-6). This study clarifies whether the enhancement of osteogenic differentiation mediated by PMIS-200a is via promoting Wnt and BMP/TGF-β signaling. Additionally, the relationship between the transfection of PMIS-200a, miR-200a inhibition, and enhanced osteogenic differentiation is studied, which provides information to optimize the delivery system using PEI nanoparticles of PMIS-200a.

miR-200a inhibits osteogenic differentiation of preosteoblasts and Pixt2 in MSCs. miR-200a was transfected into HEPM cells using a lentiviral vector. The preosteoblasts with miR-200a expression were cultured in osteogenic differentiation medium for up to 2 weeks. The biomarkers of osteogenic differentiation, including ALP and calcium content, were significantly reduced in the cells with miR-200a overexpression, compared to control cells, even when the cells were cultured with BMP-2. Runx2 mRNA was down-regulated approximately twofold (FIG. 22D). Human MSCs were cultured in 6-well plates and treated with overnight plasmid miR-200a at 5 ug/per wells. After 72 hours, the expression of miR-200a was approximately fourfold higher than the controls treated with the empty vector. Pixt-2 mRNA was significantly lower in the cells with miR-200a overexpression (FIG. 22E).

Figures 23A, 23B:
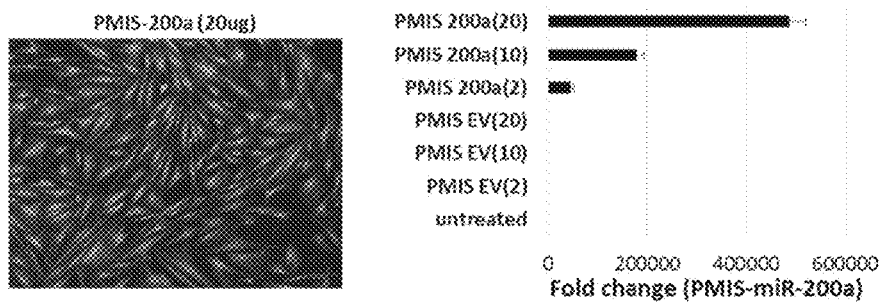
FIGS. 23A-23D. Transfection of PMIS-200a in vitro.
Figures 23C, 23D:
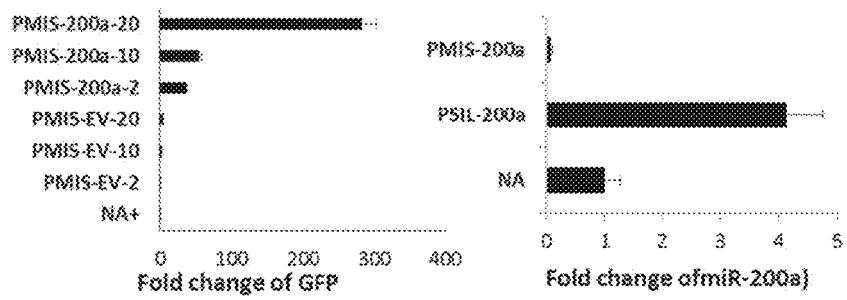

PMIS-200a transfection into bone marrow MSCs in vitro. PMIS-200a or PMIS-empty vector (EV) were prepared as described in our previous studies. Human MSCs were treated with PMIS-200a or PMIS-EV as controls at 2, 10, and 20 µg/mL using serum-free medium (Opti-MEM) for 24h. No toxicity using PMIS-200a was observed using the LIVE/DEAD® Viability/Cytotoxicity Kit (FIG. 23A). After 1 week, dose-dependent overexpression of PMIS-200a and GFP were observed (FIGS. 23B and 23C). To detect PMIS-200a, human MSCs were treated with miR-200a (psil-200a) and PMIS-200a at 1 µg/mL. After 1 week, miR-200a in human MSCs was significantly inhibited by PMIS-200a compared to untreated MSCs, while miR-200a was up-regulated in cells treated with plasmid miR-200a (psil-200a) (FIG. 23D). These data show that PMIS-200a can be safely transfected to primary human bone marrow MSCs using "NAKED" plasmid DNA to effectively inhibit miR-200a.

Figures 24A, 24B, 24C:
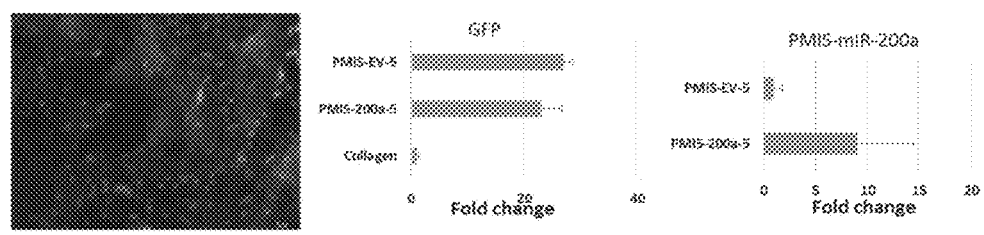
FIGS. 24A-24F. PMIS-200a can be transfected in vivo and enhance bone regeneration in rat calvarial defects.
Figures 24D, 24E, 24F:
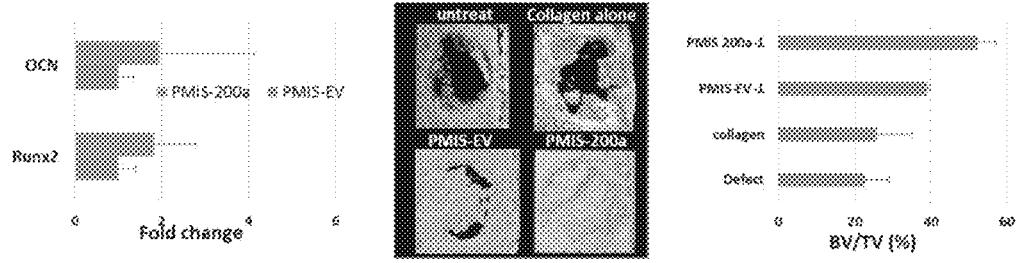

PMIS-200a can be transfected in vivo and PMIS-200a loaded collagen sponge improves bone formation in vivo: PMIS-200a was adsorbed by a collagen sponge and implanted in calvarial defects in SD rats. The four treatment groups: 1) empty defect without treatment; 2) collagen scaffold; 3) PMIS-EV (5 µg/per defect), and 4) PMIS-200a (5 µg/per defect) were randomly implanted into the defects. Rats were euthanized after 1 or 4 weeks. To determine transfection and osteogenic differentiation, the collagen sponges were harvested after 1 week. IHC showed that GFP was positive in the collagen sponges with PMIS-200a and PMIS-EV (FIG. 24A). Real-time PCR revealed that GFP expression was higher in the sponges loaded with PMIS-200a and PMIS-EV compared to the collagen sponge alone (FIG. 24B). PMIS-200a RNA was also higher in the sponges loaded with PMIS-200a compared to the PMIS EV (FIG. 24C). The transcripts of Runx2 and OCN were higher in the sponges of PMIS-200a compared to PMIS-EV (FIG. 24D). After 4 weeks, the µCT scans revealed an increase in the mineralized bone matrix in the defects treated with PMIS-200a (FIG. 24E). The BV/TV in the defects treated with PMIS-200a was more than twofold higher in defects with the untreated defect, or when treated with an empty sponge. It was also higher than the sponge loaded with PMIS-EV.

Research Procedures:

Molecular function of PMIS-200a on Wnt and TGF signaling. Primary human bone marrow MSCs and preosteoblasts HPEM are used to determine the function of PMIS-200a. The PMIS-200a is transfected into human MSCs and HPEM cells using lentiviral vectors and the cells with PMIS-200a expression are sorted using a flow cytometer. After 72 hours, the RNA is isolated from cells using the Qiagen miRNA easy kit and cDNA from those RNAs are generated using Biorads PrimePCR cDNA kit and validated the quality of the cDNA by qPCR. The Biorad PrimePCR assay system is used to detect variations of Wnt and TGF/BMP signaling (Bio-Rad). QPCR is run on control and test plates using SYBR and manufactured recommended conditions. Each plate is compared using Biorad CFX manager 3.1 and any gene showing a 2 fold increase of reduction will be further tested a validated by Q PCR primer probe set for that gene. In addition, TOP/FOP flash is transfected in the MSCs and HPEM with overexpression of PMIS-200a. The luciferase activity of the reporter gene using TOP/FOP flash analysis is further used to determine the roles of PMIS-200a in the Wnt activity.

RNA-seq and bioinformatics analysis of PMIS-200a. HEPM cells and primary human MSCs are used to run the RNA sequencing and bioinformatics analysis. PMIS-200a is transfected into HEPM and human MSCs using lentiviral vectors. The RNA-seq and Bioinformatics analysis will be performed as described above.

Correlation between PMIS-200a, miR-200a, and osteogenic differentiation. Initial studies demonstrated that the transfection of PMIS-200a was in a dose-dependent manner in human MSCs after treatment with naked plasmid DNA. In this study, it is tested whether miR-200a inhibition correlates to PMIS-200a treatment and it is determined how osteogenic differentiation and miR-200a is varied by PMIS-200a. Human MSCs are treated with a concentration of plasmid PMIS-200a at 0, 1, 5, 25, 50 µg/per well. The expression of miR-200a and PMIS-200a is quantitatively measured using real-time PCR after 24, 48, and 72 hours. The cells with different treatment are subsequently exposed to osteogenic differentiation medium for up to 2 weeks. The expression of PMIS-200a, miR-200a, and biomarkers of osteogenic differentiation, including ALP, Runx2, collagen type I, OCN, BSP, and Osterix transcripts are quantified using real-time PCR after 4 and 7 days. Additionally, ALP activity, protein levels of OCN, BSP, and collagen type 1, and calcium content of transfected MSCs are quantified after 1 and 2 weeks.

Delivery system using PEI for PMIS-200a transfection. A wide range of N/P ratios are investigated on the encapsulation efficiency, cytotoxicity, and transfection efficiency of PMIS-200a and osteogenic differentiation. PEI nanoparticles encapsulating plasmid PMIS-200a, with a range of N/P ratios (1, 5, 10, 16, and 21), are synthesized. The characteristics of PEI-PMIS-200a nanoplexes will be determined. To test cytotoxicity, human bone marrow MSCs (Lonza) are seeded at 10,000 cells/per well in a 96-well plate and treated with PEI-PMIS-200a nanoplexes at different N/P ratios. The cytotoxicity of PEI-PMIS-200a nanoplexes are determined using MTT assay after 4 and 24 hrs. To test transfection efficiency human MSCs are treated with 1 µg of PEI-PMIS-200a nanoplexes with different N/P ratios. The expression of PMIS-200a and miR-200a is determined by real-time PCR after 24, 48, and 72 hrs. To test osteogenic differentiation of human MSCs varied by PMIS-200a transfection using PEI nanoparticles, the cells in a 6-well plate are treated with PEI alone, PEI-PMIS-200a nanoplexes, and PEI-PMIS-empty vector nanoplexes at 1, 2, 5, 10 µg at a N/P ratio of 10. If warranted, the N/P ratio of PEI-miR-200c is adjusted based on the studies performed to determine transfection efficiency and cytotoxicity. The cells are then cultured in osteogenic medium for up to 2 weeks. The expression of PMIS-200a, miR-200a and the biomarkers of osteogenic differentiation are quantified.

Potential synergism of PMIS-200a and miR-200c: Human MSCs in a 6-well plate are treated with different combinations of PMIS-200a together with miR-200c. Naked plasmid DNA and PMIS-200a and miR-200c incorporated into PEI nanoplexes are used. The dose of PMIS-200a and miR-200c at 1 µg/per well is used, respectively. Empty vectors serve as controls. The N/P ratio and doses of miR-200c and PMIS-200a may be adjusted as needed. The cells are then differentiated and the biomarkers of osteogenic differentiation are analyzed.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of stimulating osteogenic differentiation in a patient in need thereof, comprising administering to the patient a therapeutic composition comprising
   (a) miR-200c or a first expression cassette expressing miR-200c, and
   (b) a second expression cassette comprising a second promoter operably linked to a plasmid-based miR-200a inhibitor (PMIS-200a);
      wherein the therapeutic composition stimulates stimulating osteogenic differentiation in the patient,
      wherein the therapeutic composition comprises the first expression cassette expressing miR-200c, wherein the miR-200c is operably linked to a first promoter.

2. The method of claim 1, wherein the first promoter is transiently expressed or is constitutively expressed.

3. The method of claim 1, wherein the first promoter is a tissue-specific or inducible promoter.

4. A method of stimulating osteogenic differentiation in a patient in need thereof, comprising administering to the patient a therapeutic composition comprising
   (a) miR-200c or a first expression cassette expressing miR-200c, and
   (b) a second expression cassette comprising a second promoter operably linked to a plasmid-based miR-200a inhibitor (PMIS-200a);
      wherein the therapeutic composition stimulates stimulating osteogenic differentiation in the patient,
      wherein the first expression cassette is contained in a first vector.

5. The method of claim 4, wherein the first vector is a first plasmid.

6. A method of stimulating osteogenic differentiation in a patient in need thereof, comprising administering to the patient a therapeutic composition comprising
   (a) miR-200c or a first expression cassette expressing miR-200c, and
   (b) a second expression cassette comprising a second promoter operably linked to a plasmid-based miR-200a inhibitor (PMIS-200a);
      wherein the therapeutic composition stimulates stimulating osteogenic differentiation in the patient,
      wherein the therapeutic composition comprises the second expression cassette, and
      wherein the PMIS-200a is operably linked to a second promoter, wherein the second expression cassette is contained in the first vector.

7. The method of claim 6, wherein the second expression cassette is contained in a second vector.

8. The method of claim 7, wherein the second vector is a second plasmid.

9. The method of claim 6, wherein the second promoter is a tissue-specific or inducible promoter.

10. The method of claim 1, wherein the osteogenic differentiation bone generates oral, craniofacial, calvarial and/or periodontal bone.

11. The method of claim 1, wherein the therapeutic composition is contained in biodegradable nanoparticle material.

12. The method of claim 11, wherein the biodegradable nanoparticle material is polyethylenimine (PEI).

13. The method of claim 11, wherein the biodegradable nanoparticle material is polylactide-co-glycolide (PLGA).

14. The method of claim 1, wherein the therapeutic composition is contained in a collagen sponge.

15. The method of claim 1, wherein the therapeutic composition is administered locally.

16. The method of claim 1, wherein the therapeutic composition is a sustained release formulation.

* * * * *

SEQUENCE LISTING

```
<160> NUMBER OF SEQ ID NOS: 3

<210> SEQ ID NO 1
<211> LENGTH: 23
<212> TYPE: RNA
<213> ORGANISM: Homo sapiens

<400> SEQUENCE: 1
caagcaacuu uuguacagua uuu                                            23

<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agguaguaau gggccgucau aau                                            23
```

```
<210> SEQ ID NO 3
<211> LENGTH: 23
<212> TYPE: RNA
<213> ORGANISM: Homo sapiens

<400> SEQUENCE: 3
ugccagaaga gaauucagua uuu                                            23
```